US007270951B1

(12) United States Patent
Stemple et al.

(10) Patent No.: US 7,270,951 B1
(45) Date of Patent: Sep. 18, 2007

(54) METHOD FOR DIRECT NUCLEIC ACID SEQUENCING

(75) Inventors: Derek L. Stemple, Hertfordshire (GB); Niall A. Armes, Cambridge (GB)

(73) Assignee: ASM Scientific, Inc., Cambridge, MA (US)

( * ) Notice: Subject to any disclaimer, the term of this patent is extended or adjusted under 35 U.S.C. 154(b) by 0 days.

(21) Appl. No.: 09/936,095

(22) PCT Filed: Mar. 10, 2000

(86) PCT No.: PCT/GB00/00873

§ 371 (c)(1),
(2), (4) Date: Jun. 6, 2002

(87) PCT Pub. No.: WO00/53805

PCT Pub. Date: Sep. 14, 2000

Related U.S. Application Data

(63) Continuation-in-part of application No. 09/266,187, filed on Mar. 10, 1999.

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.1; 536/24.3

(58) Field of Classification Search ............ 435/6, 435/91.2; 536/23.1, 24.3
See application file for complete search history.

(56) References Cited

U.S. PATENT DOCUMENTS

| 4,811,218 A | 3/1989 | Hunkapiller et al. | |
|---|---|---|---|
| 5,171,534 A | 12/1992 | Smith et al. | |
| 5,302,509 A | 4/1994 | Cheeseman | |
| 5,405,747 A | 4/1995 | Jett et al. | |
| 5,547,839 A | 8/1996 | Dower et al. | |
| 5,716,825 A | 2/1998 | Hancock et al. | |
| 5,728,529 A | 3/1998 | Metzker et al. | |
| 5,798,210 A | 8/1998 | Canard et al. | |
| 5,821,058 A | 10/1998 | Smith et al. | |
| 5,846,727 A | 12/1998 | Soper et al. | |
| 5,853,668 A | 12/1998 | Begg et al. | |
| 5,856,174 A | 1/1999 | Lipshutz et al. | |
| 5,858,671 A | 1/1999 | Jones | |
| 5,919,626 A | 7/1999 | Shi et al. | |
| 6,007,987 A | 12/1999 | Cantor et al. | 435/6 |
| 6,136,543 A | 10/2000 | Anazawa et al. | |
| 6,210,896 B1 | 4/2001 | Chan | |
| 6,255,083 B1 * | 7/2001 | Williams | 435/6 |

FOREIGN PATENT DOCUMENTS

| GB | 2 102 005 A | 1/1983 | |
|---|---|---|---|
| WO | WO90/13666 | 11/1990 | |
| WO | WO 91/06678 | 5/1991 | |
| WO | WO91/06678 | * 5/1991 | |
| WO | WO93/21340 | 10/1993 | |
| WO | WO94/21822 | 9/1994 | |
| WO | WO96/31622 | 10/1996 | |
| WO | WO98/33939 | 8/1998 | |
| WO | WO 99/05315 | 2/1999 | |
| WO | WO99/05315 | * 2/1999 | |
| WO | WO 00/36152 | 6/2000 | |

OTHER PUBLICATIONS

Brandis et al. "Slow Rate of Phosphodiester Bond Formation Accounts for the Strong Bias that Taq DNA Polymerase Shows against 2',3'-Dideoxymucleotide Terminators.:" Biochemistry 35: 2189-2200 (1996).
Burns et al. "An Integrated Nanoliter DNA Analysis Device." Science 282: 484-487 (1998).
Chan and Nie "Quantum Dot Bioconjugates for Ultrasensitive Nonisotopic Detection." Science 281: 2016-2018 (1998).
Dickson et al. "On/off blinking and Switching Behaviour Of Single Molecules of Green Fluorescent Protein." Nature 388: 355-358 (1997).
Dickson et al. "Three-Dimensional Imaging of Single Molecules Solvated in Pores of Poly(acrylamide) Gels." Science 274: 966-971 (1996).
Dovichi et al. "DNA Sequencing By Capillary Electrophoresis." Electrophoresis 18: 2393-2399 (1997).
Gordon et al. "Quantitative Fluorescence Resonance Energy Transfer Measurements Using Fluorescence Microscopy." Biophys. J. 74: 2702-2713 (1998).
Ha et al. "Probing The Interaction Between Two Single Molecules: Fluorescence Resonance Energy Transfer Between A Single Donor And A Single Acceptor." Proc. Natl. Sci. USA 93: 6264-6268 (1996).
Hacia, "Resequencing and Mutational Analysis Using Oligonucleotide Microarrays." Nature Genetics Supp. 21: 42-47 (1999).
Harada, et al. "Single-Molecule Imaging of RNA Polymerase-DNA Interactions in Real Time." Biophys. J. 76: 709-715 (1999).
Hiratsuka et al. "New Ribose-Modified Fluorescent Analogs of Adenine and Guanine Nucleotides Available as Substrates for Various Enzymes." Biocchim Biophys Acta 742: 496-508 (1983).
Idury and Waterman, "A New Algorithm for DNA Sequence Assembly." J. Comput. Biol. 2: 291-306 (1995).
Ishijima et al. "Simultaneous Observation of Individual ATPase and Mechanical Events by a Single Myosin Molecule During Interaction with Actin." Cell 92: 161-171 (1998).

(Continued)

Primary Examiner—Teresa E. Strzelecka
(74) Attorney, Agent, or Firm—Mintz, Levin, Cohn, Ferris, Glovsky and Popeo, P.C.

(57) ABSTRACT

The present invention provides a novel sequencing apparatus and the methods employed to determine the nucleotide sequence of many single nucleic acid molecules simultaneously, in parallel. The methods and apparatus of the present invention offer a rapid, cost effective, high throughput method by which nucleic acid molecules from any source can be readily sequenced without the need for prior amplification of the sample or prior knowledge of any sequence information.

13 Claims, 8 Drawing Sheets

OTHER PUBLICATIONS

Iwane et al. "Single Molecular Assay of Individual ATP Turnover by a Myosin-GFP Fusion Protein Expressed In Vitro." FEBS Lett. 407: 235-238 (1998).

Izawa et al. "Recognition Sites of 3'-OH Group by T7 RNA Polymerase and Its Application to Transcriptional Sequencing." J. Biol. Chem. 273: 14242-14246 (1998).

Keller et al. "Single-Moleccule Fluorescence Analysis in Solution." Applied Spectroscopy 50: 12A-32A 1996.

Kricka, "Miniaturization of Analytical Systems." Clinical Chemistry 44:9: 2008-2014 (1998).

Luckey et al. "High Speed DNA Sequencing By Capillary Electrophoresis," Nucleic Acids Res 18: 4417-4421 (1990).

Mertz et al. "Single-Molecule Detection By Two-Photon-Excited Fluorescence." Opt. Lett. 20:2532-2534 (1995).

Metzker et al. "Termination Of DNA Synthesis by Novel 3'-Modified-Deoxyribonucleoside 5'-Triphosphates." Nucleic Acids Res. 22: 4259-4267 (1994).

Metzker et al. "Elimination of Residual Natural Nucleotides from 3'-O-Modified-dNTP Syntheses by Enzymatic Mop-Up." BioTechniques 25.5: 814-817 (1998).

Metzker et al. "Quantitation of Mixed-Base Populations of HIV-1 Variants by Automated DNA Sequencing with BODIPY® Dye-Labeled Primers." Bio Techniques 25.3: 446-462 (1998).

Nie et al. "Probing Individual Molecules with Confocal Fluorescence Microscopy." Science 266: 1018-1021 (1994).

Nie and Zare, "Optical Detection of Single Molecules." Annu. Rev. Biophys. Biomol. Struct. 26: 567-596 (1997).

Orita et al. "Rapid and Sensitive Detection of Point Mutations and DNA Polymorphisms Using the Polymearse Chain Reaction." Genomics 5: 874-879 (1989).

Pierce et al. "Imaging Individual Green Fluorescent Proteins." Nature 388: 338 (1997).

Prober et al. "A System for Rapid DNA Sequencing With Fluorescent Chain-Terminating Dideoxynucleotides." Science 238: 336-341 (1987).

Rawlinson et al. "Analysis of the Complete DNA Sequence of Murine Cytomegalovirus." J. Virol 70: 8833-8849 (1996).

Smith et al. "Fluorescence Detection in Automated DNA Sequence Analysis." Nature 321: 674-679 (1986).

Sutton et al. "TIGR Assembler: A New Tool for Assembling Large Shotgun Sequencing Projects." Genome Sci. Technol. 1: 9-19 (1995).

Tokunaga et al. "Single Molecule Imaging of Fluorophores and Enzymatic Reactions Achieved by Objective-Type Total Internal Reflection Fluorescence Microscopy." Biochem. Biophys. Res. Comm. 235: 47-53 (1997).

Venter et al. "Shotgun Sequencing of the Human Genome." Science 280:1540-1545 (1998).

Wang et al. "Force and Velocity Measured for Single Molecules of RNA Polymerase." Science 282: 902-907 (1998).

Yin et al. "Transcription Against an Applied Force." Science 270: 1653-1657 (1995).

International Search Report for PCT/GB00/00873 dated Aug. 18, 2000.

Wang et al. "Discontinuous Movements of DNA and RNA Polymerase Accompany Formation of a Paused Transcription Complex"; *Cell*, 81:341-350 (1995).

* cited by examiner

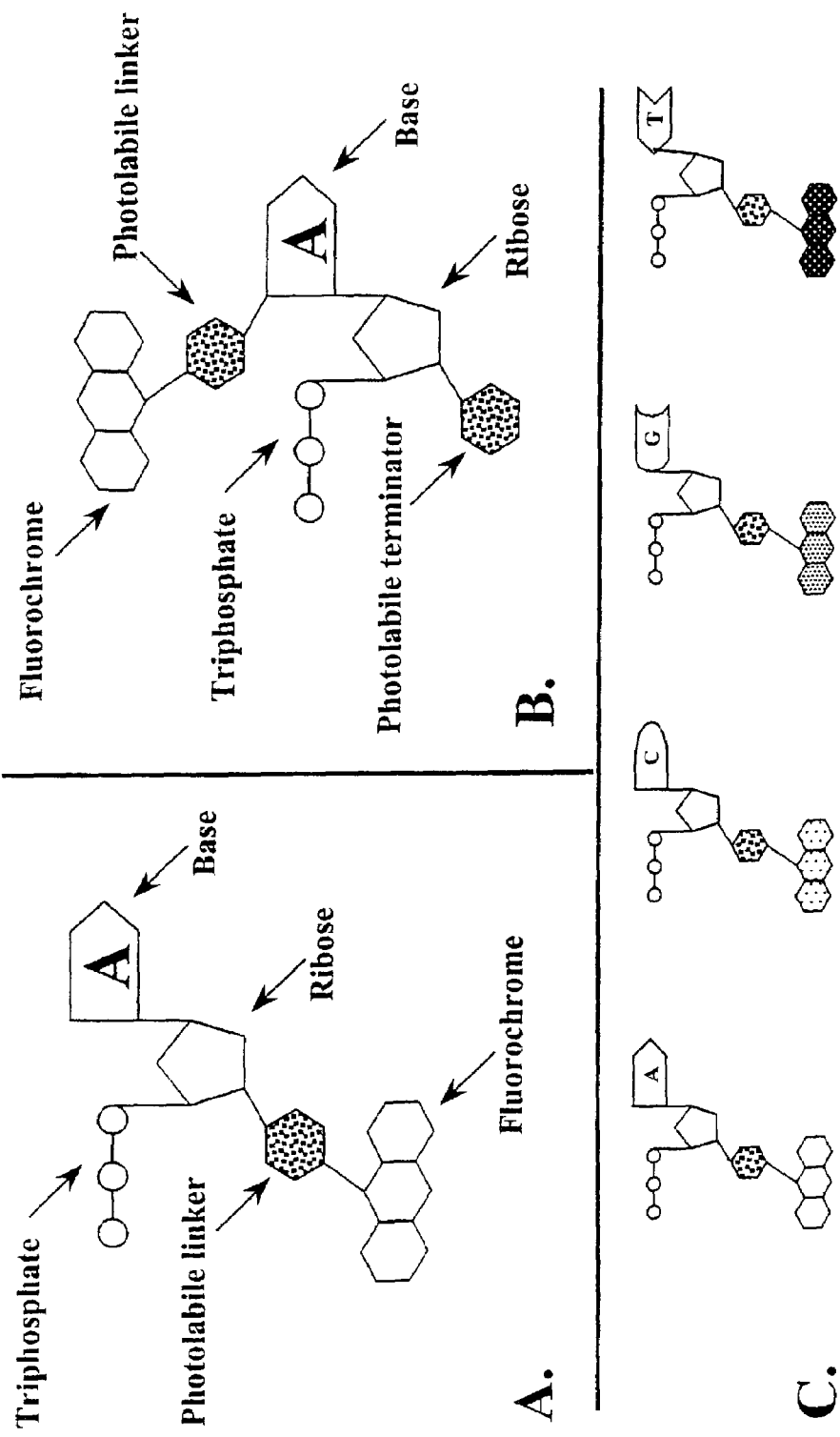
FIG. 1 Example Modified Nucleotides for DNAS

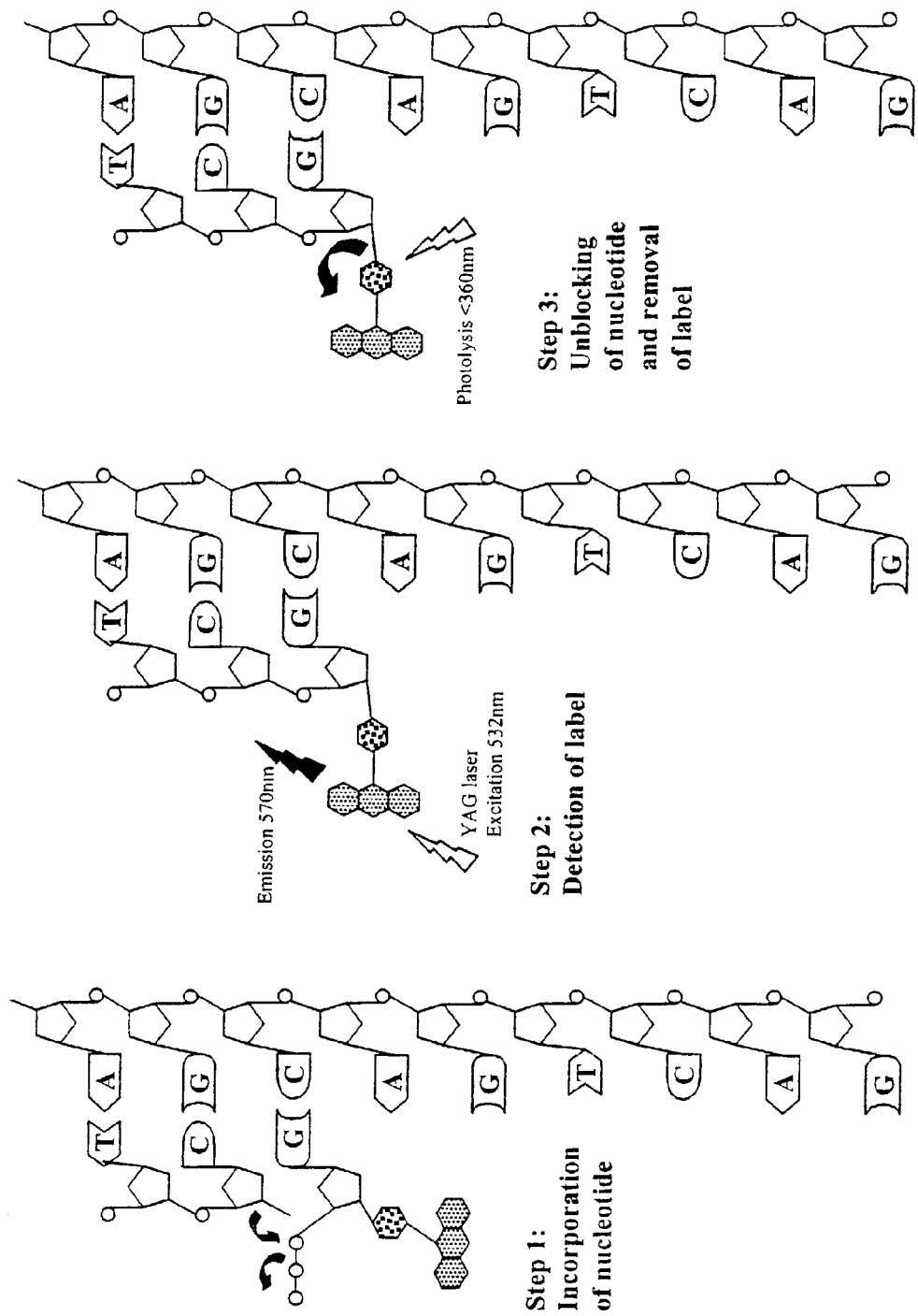
FIG. 2 The DNAS Reaction Cycle

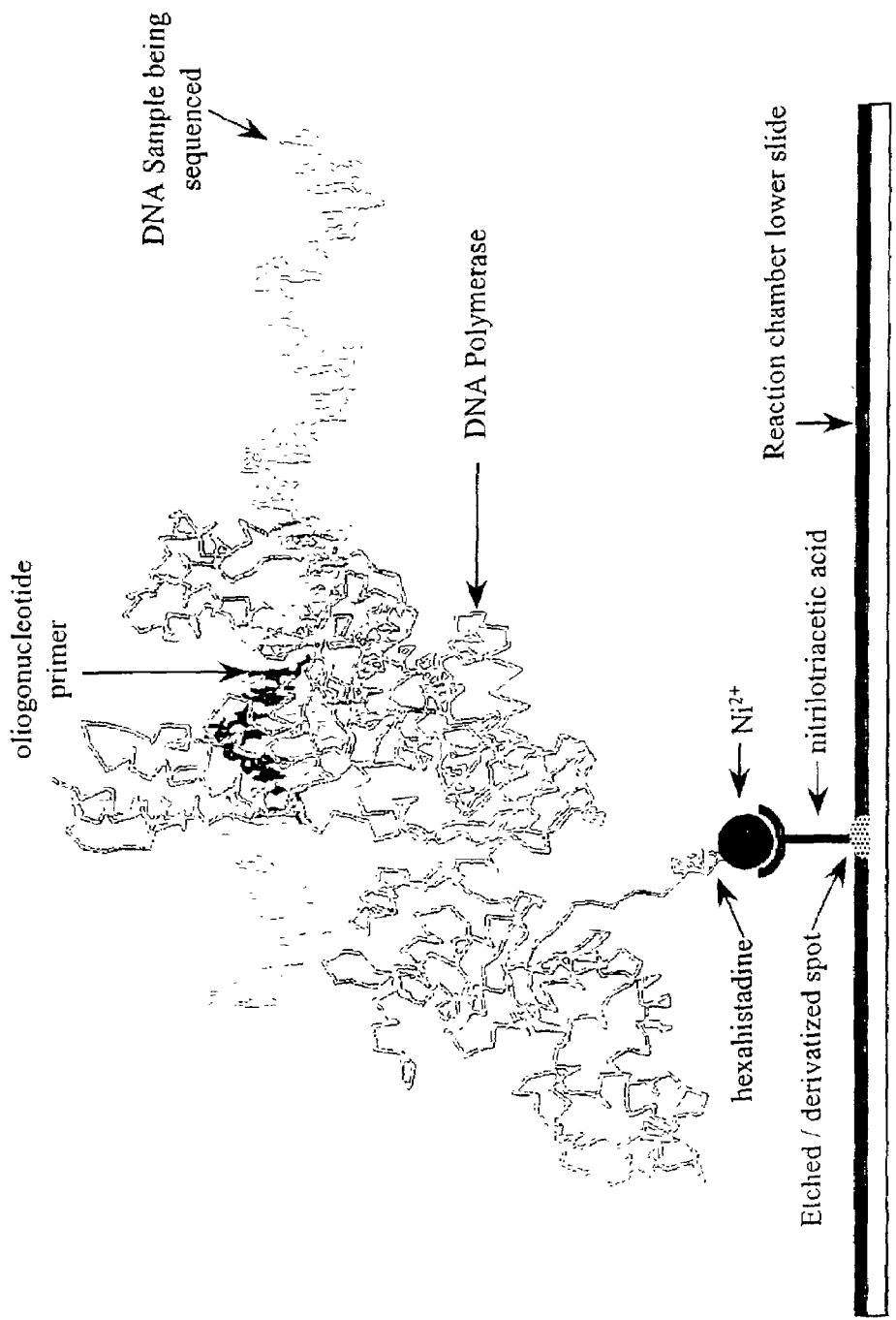
FIG. 3 Example of a DNAS Reaction Center

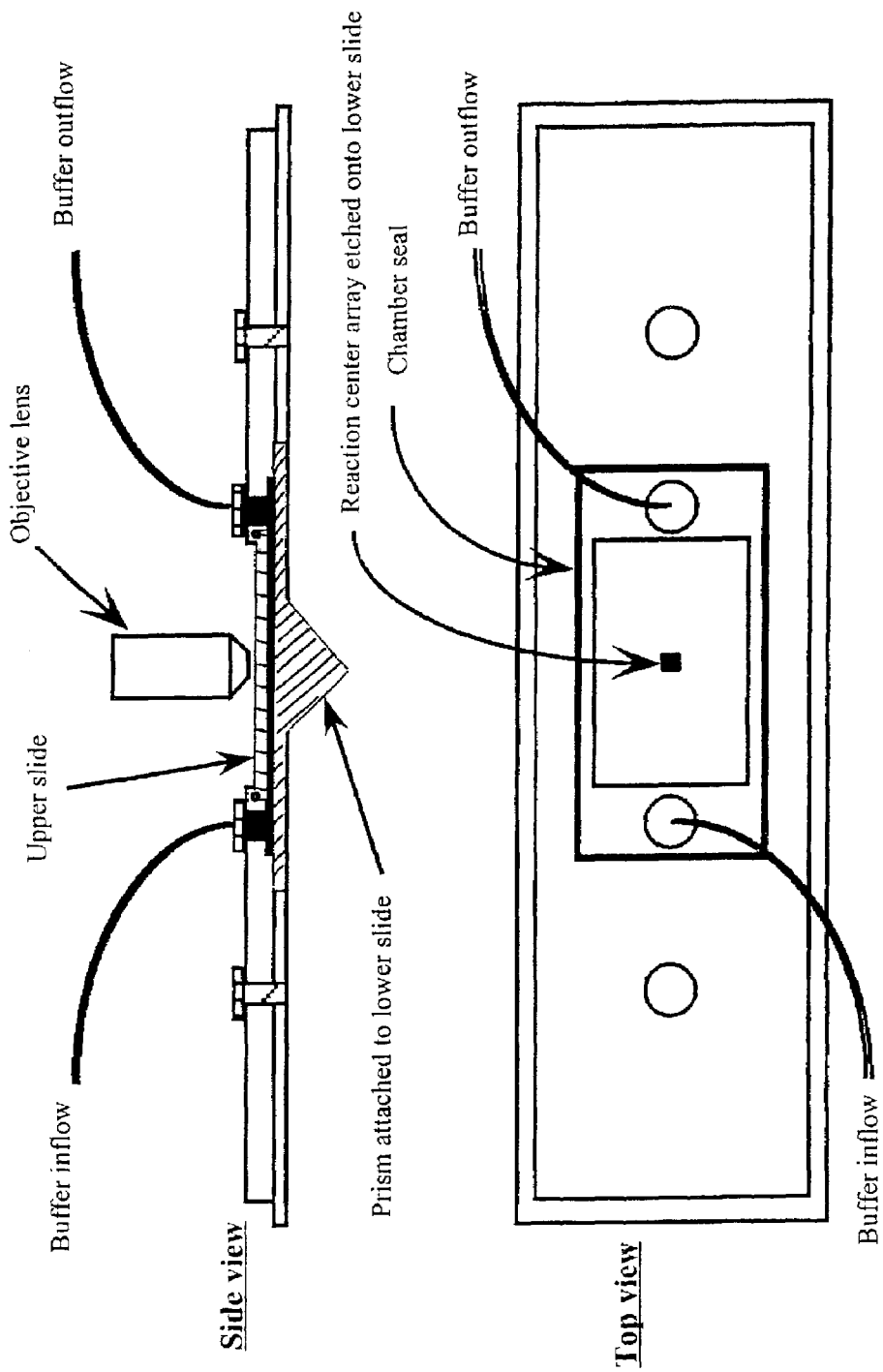
FIG. 4 DNAS Reaction chamber assembly

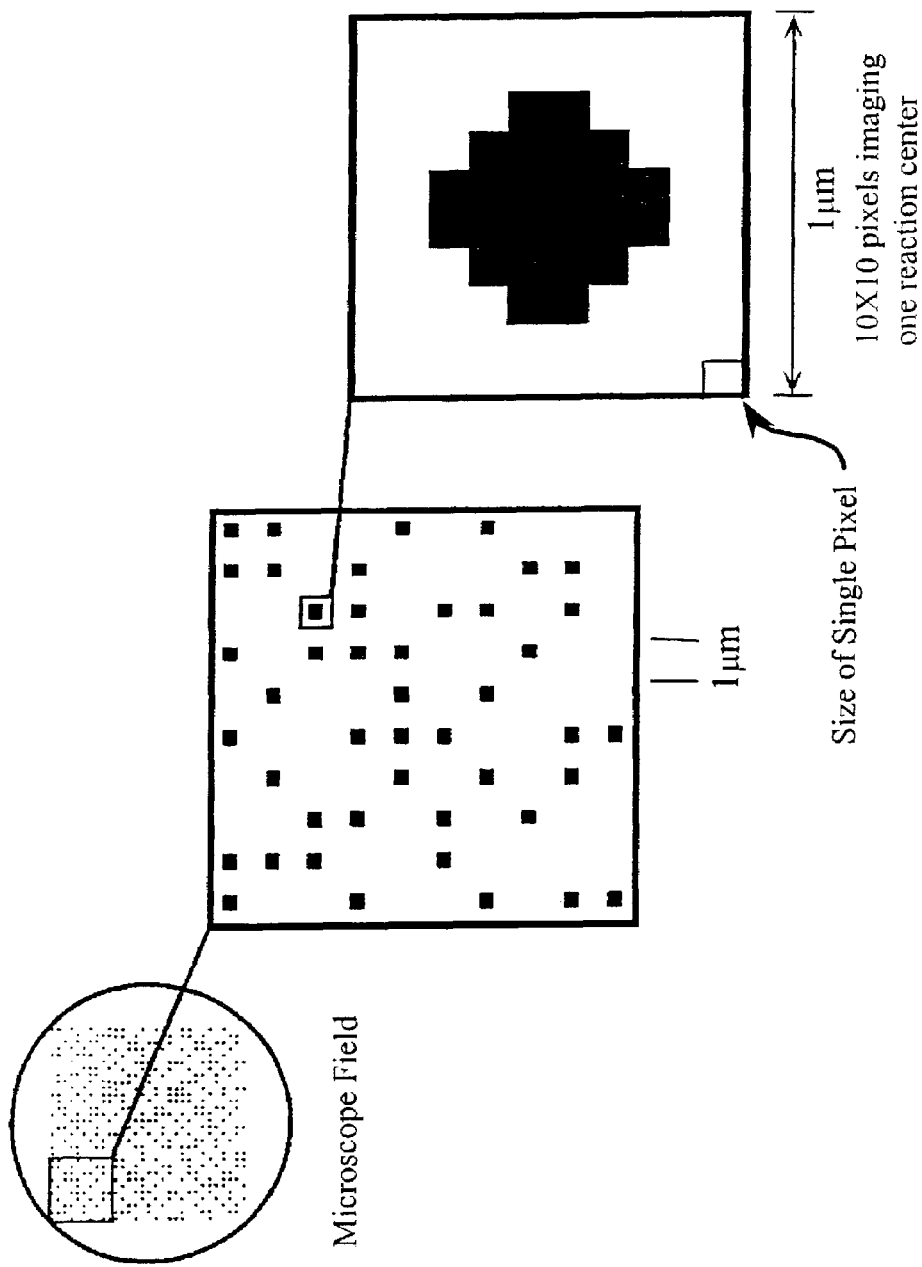
FIG. 5 Diagram of DNAS Reaction Center Array

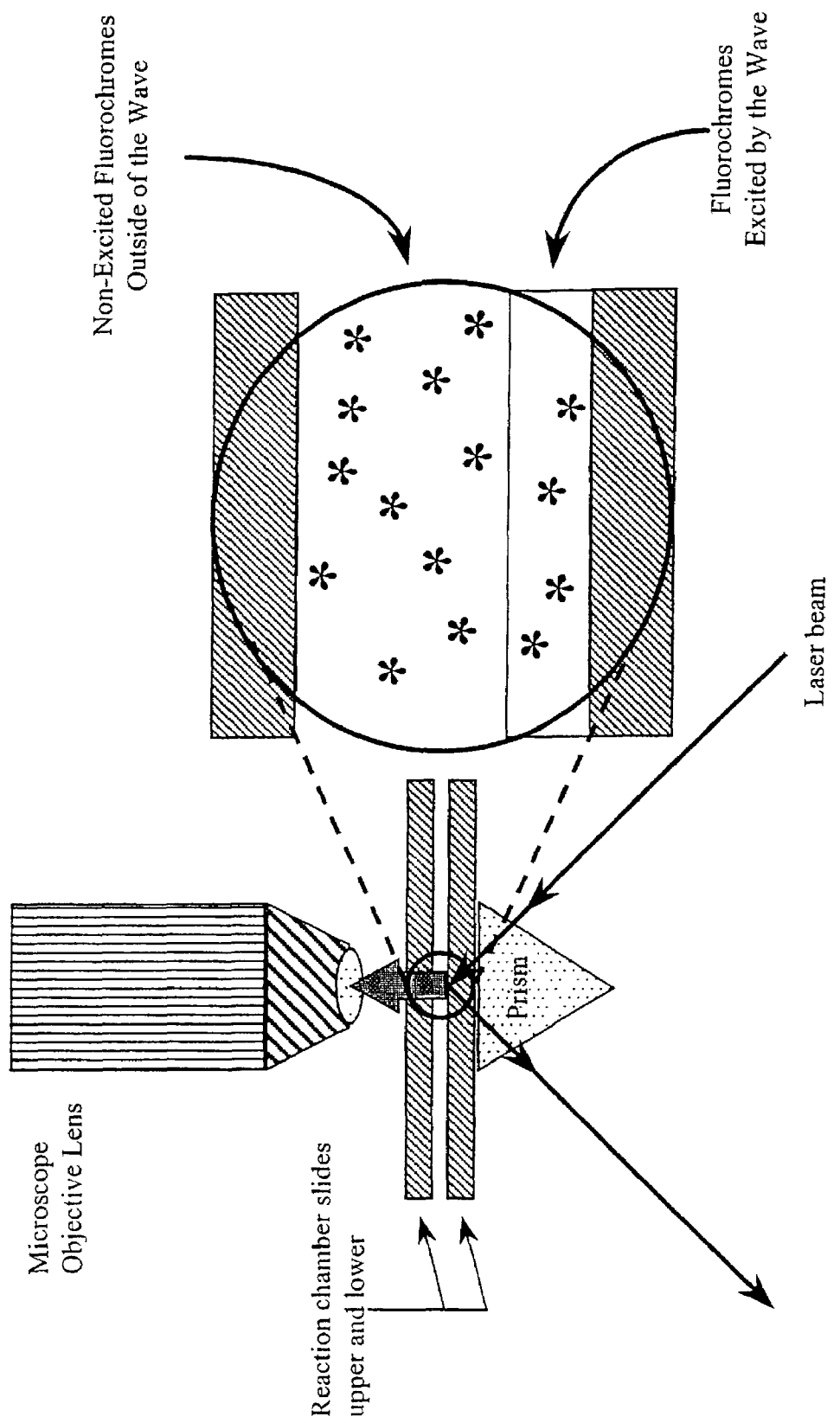
FIG. 6 Principle of the Evanescent Wave

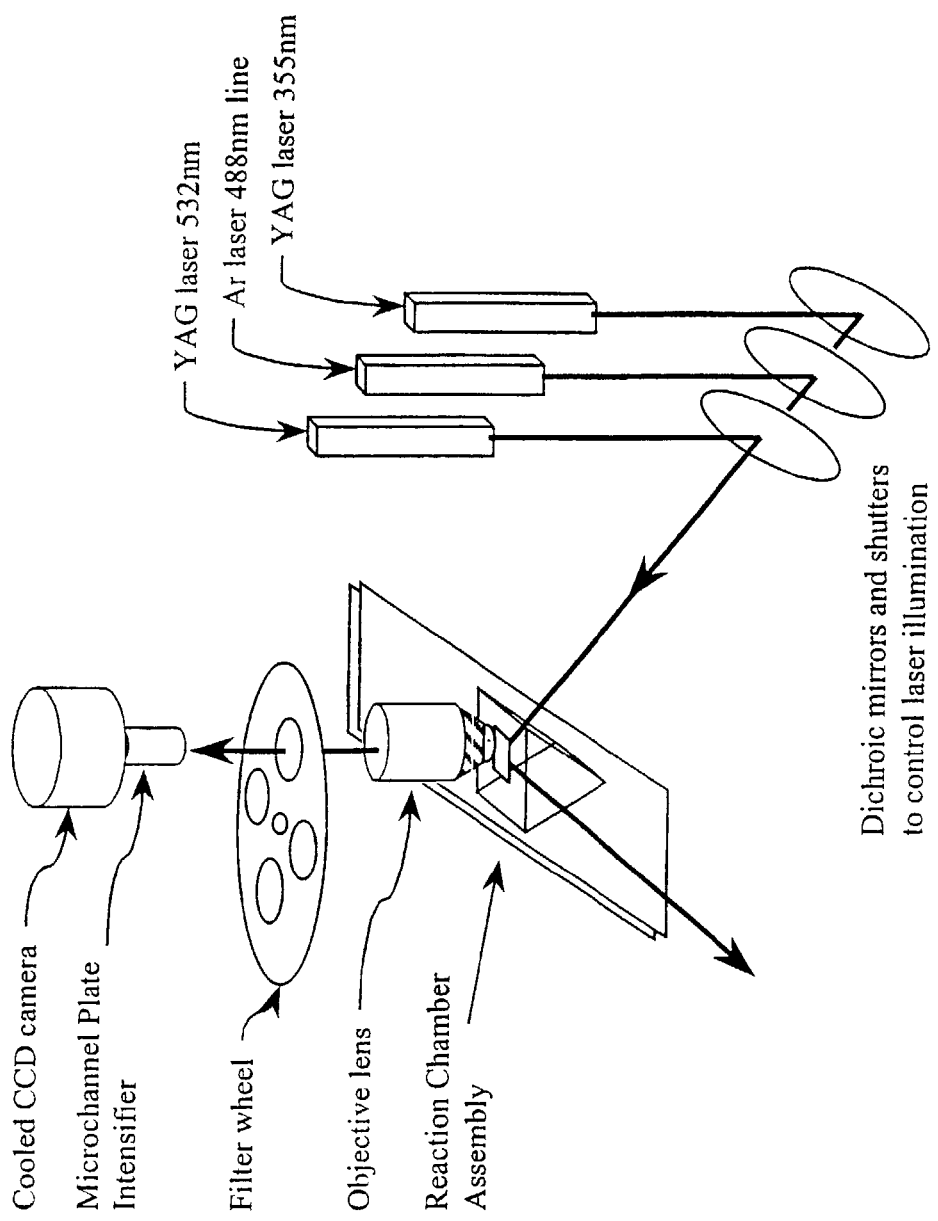
FIG. 7 Setup for DNAS using TIRFM

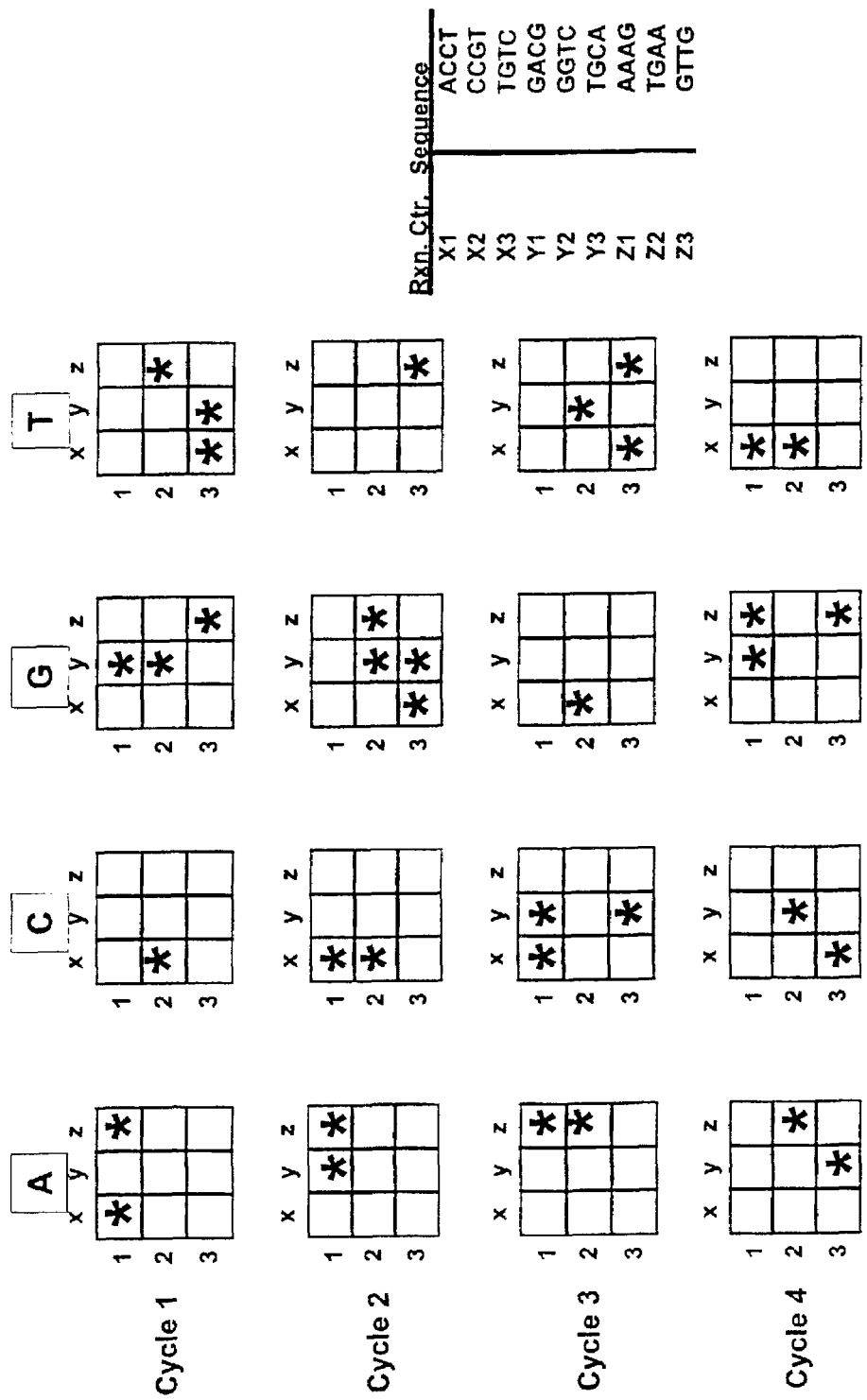
FIG. 8 DNAS Data Acquisition: A 3x3 Matrix Example

METHOD FOR DIRECT NUCLEIC ACID SEQUENCING

This application is a national stage of International Application Number PCT/GB00/00873 filed Mar. 10, 2000 which is a continuation-in-part of U.S. application Ser. No. 09/266,187 filed Mar. 10, 1999.

FIELD OF THE INVENTION

The present invention relates to methods for sequencing nucleic acid samples. More specifically, the present invention relates to methods for sequencing without the need for amplification; prior knowledge of some of the nucleotide sequence to generate the sequencing primers; and the labor-intensive electrophoresis techniques.

BACKGROUND OF THE INVENTION

The sequencing of nucleic acid samples is an important analytical technique in modern molecular biology. The development of reliable methods for DNA sequencing has been crucial for understanding the function and control of genes and for applying many of the basic techniques of molecular biology. These methods have also become increasingly important as tools in genomic analysis and many non-research applications, such as genetic identification, forensic analysis, genetic counseling, medical diagnostics and many others. In these latter applications, both techniques providing partial sequence information, such as fingerprinting and sequence comparisons, and techniques providing full sequence determination have been employed. See, e.g., Gibbs et al., *Proc. Natl. Acad. Sci. USA* 86: 1919-1923 (1989); Gyllensten et al., *Proc. Natl. Acad. Sci. USA* 85: 7652-7656 (1988); Carrano et al., *Genonmics* 4: 129-136 (1989); Caetano-Annoles et al., *Mol. Gen. Genet.* 235: 157-165 (1992); Brenner and Livak, *Proc. Natl. Acad. Sci. USA* 86: 8902-8906 (1989); Green et al., *PCR Methods and Applications* 1: 77-90 (1991); and Versalovic et al., *Nucleic Acid Res.* 19: 6823-6831 (1991).

Most currently available DNA sequencing methods require the generation of a set of DNA fragments that are ordered by length according to nucleotide composition. The generation of this set of ordered fragments occurs in one of two ways: (1) chemical degradation at specific nucleotides using the Maxam-Gilbert method or (2) dideoxy nucleotide incorporation using the Sanger method. See Maxam and Gilbert, *Proc Natl Acad Sci USA* 74: 560-564 (1977); Sanger et al. *Proc Natl Acad Sci USA* 74: 5463-5467 (1977). The type and number of required steps inherently limits both the number of DNA segments that can be sequenced in parallel, and the amount of sequence that can be determined from a given site. Furthermore, both methods are prone to error due to the anomalous migration of DNA fragments in denaturing gels. Time and space limitations inherent in these eel-based methods have fueled the search for alternative methods.

In an effort to satisfy the current large-scale sequencing demands, improvements have been made to the Sanger method. For example, the use of fluorescent chain terminators simplifies detection of the nucleotides. The synthesis of longer DNA fragments and improved fragment resolution produces more sequence information from each experiment. Automated analysis of fragments in gels or capillaries has significantly reduced the labor involved in collecting and processing sequence information. See, e.g., Prober et al., *Science* 238: 336-341 (1987); Smith et al., *Nature* 321: 674-679 (1986); Luckey et al., *Nucleic Acids Res* 18: 4417-4421(1990); Dovichi, *Electrophoresis* 18: 2393-2399 (1997).

However current DNA sequencing technologies still suffer three major limitations. First, they require a large amount of identical DNA molecules, which are generally obtained either by molecular cloning or by polymerase chain reaction (PCR) amplification of DNA sequences. Current methods of detection are insensitive and thus require a minimum critical number of labeled oligonucleotides. Also, many identical copies of the oligonucleotide are needed to generate a sequence ladder. A second limitation is that current sequencing techniques depend on priming from sequence-specific oligodeoxynucleotides that must be synthesized prior to initiating the sequencing procedure. Sanger and Coulson, *J. Mol. Biol.* 94: 441-448 (1975). The need for multiple identical templates necessitates the synchronous priming of each copy from the same predetermined site. Third, current sequencing techniques depend on lengthy, labor-intensive electrophoresis techniques that are limited by the rate at which the fragments may be separated and are also limited by the number of bases that can be sequenced in a given experiment by the resolution obtainable on the gel.

In an effort to dispense with the need for electrophoresis techniques, a sequencing method was developed which uses chain terminators that can be uncaged, or deprotected, for further extension. See, U.S. Pat. No. 5,302,509: Metzker et al. *Nucleic Acids Res.* 22: 4259-4267 (1994). This method involves repetitive cycles of base incorporation, detection of incorporation, and re-activation of the chain terminator to allow the next cycle of DNA synthesis. Thus, by detecting each added base while the DNA chain is growing, the need for size-fractionation is eliminated. This method is nevertheless still highly dependent on large amounts of nucleic acid to be sequenced and the use of known sequences for priming the initiation of chain or growth. Moreover, this technique is plagued by any inefficiencies of incorporation and deprotection. Because incorporation and 3'-OH regeneration are not completely efficient. a pool of initially identical extending strands can rapidly become asynchronous and sequences cannot be resolved beyond a few limited initial additions.

Thus, a need still remains in the art for a rapid, cost effective, high throughput method for sequencing unknown nucleic acid samples that eliminates the need for amplification; prior knowledge of some of the nucleotide sequence to generate sequencing primers; and labor-intensive electrophoresis techniques.

SUMMARY OF THE INVENTION

The present invention provides rapid, cost effective, high throughput methods for sequencing unknown nucleic acid samples that eliminate the need for amplification; prior knowledge of some of the nucleotide sequence to generate sequencing primers; and labor-intensive electrophoresis techniques. The methods of the present invention permit direct nucleic acid sequencing (DNAS) of single nucleic acid molecules.

According to the methods of the present invention, a plurality of polymerase molecules is immobilized on a solid support through a covalent or non-covalent interaction. A nucleic acid sample and oligonucleotide primers are introduced to the reaction chamber in a buffered solution containing all four labeled-caged nucleoside triphosphate terminators. Template-driven elongation of a nucleic acid is mediated by the attached polymerases using the labeled-caged nucleoside triphosphate terminators. Reaction centers are monitored by the microscope system until a majority of sites contain immobilized polymerase bound to a nucleic acid template with a single incorporated labeled-caged nucleotide terminator. The reaction chamber is then flushed with a wash buffer. Specific nucleotide incorporation is then determined for each active reaction center. Following detection, the reaction chamber is irradiated to uncage the incorporated nucleotide and flushed with wash buffer once again. The presence of labeled-caged nucleotides is once again monitored before fresh reagents are added to reinitiate synthesis, to verify that reaction centers are successfully uncaged. A persistent failure of release or incorporation, however, indicates failure of a reaction center. A persistent failure of release or incorporation consists of 2-20 cycles, preferably 3-10 cycles, more preferably 3-5 cycles, wherein the presence of a labeled-caged nucleotide is detected during the second detection step, indicating that the reaction center was not successfully uncaged. The sequencing cycle outlined above is repeated until a large proportion of reaction centers fail.

The differentially-labeled nucleotides used in the sequencing methods of the present invention have a detachable labeling group and are blocked at the 3' portion with a detachable blocking group. In a preferred embodiment, the labeling group is directly attached to the detachable 3' blocking group. Uncaging of the nucleotides can be accomplished enzymatically, chemically, or preferably photolytically, depending on the detachable linker used to link the labeling group and the 3' blocking group to the nucleotide.

In another preferred embodiment, the labeling group is attached to the base of each nucleotide with a detachable linker rather than to the detachable 3' blocking group. The labeling group and the 3' blocking group can be removed enzymatically, chemically, or photolytically. Alternative, the labeling group can be removed by a different method than and the 3' blocking group. For example, the labeling group can be removed enzymatically while the 3' blocking group is removed chemically, or by photochemical activation.

Many independent reactions occur simultaneously within the reaction chamber, each individual reaction center generating a few hundred, or thousands, of base pairs. This apparatus has the capacity to sequence in parallel thousands and possibly millions of separate templates from either specified or random sequence points. The combined sequence from each run is on the order of several million base-pairs of sequence and does not require amplification, prior knowledge of a portion of the target sequence, or resolution of fragments on gels or capillaries. Simple DNA preparations from any source can be sequenced with the apparatus and methods of the present invention.

BRIEF DESCRIPTION OF THE DRAWINGS

FIG. 1 (Panels A-C) is a schematic representation of labeled-caged terminator nucleotides for use in direct nucleic acid sequencing. Panel A depicts a deoxyadenosine triphosphate modified by attachment of a photolabile linker-fluorochrome conjugate to the 3' carbon of the ribose. Panel B depicts an alternative configuration, wherein the fluorochrome is attached to the base of the nucleotide by way of a photolabile linker. Panel C depicts the four different nucleotides each labeled with a fluorochrome with distinct spectral properties, which permits the four nucleotides to be distinguished during the detection phase of a direct nucleic acid sequencing reaction cycle.

FIG. 2 is a schematic representation of the steps of one cycle of direct nucleic acid sequencing, wherein step 1 illustrates the incorporation of a labeled-caged nucleotide, step 2 illustrates the detection of the label, and step 3 illustrates the unblocking of the 3'-OH cage.

FIG. 3 is a schematic representation of a reaction center depicting an immobilized polymerase and a nucleic acid sample being sequenced.

FIG. 4 is a schematic representation of the reaction chamber assembly that houses the array of DNAS reaction centers and mediates the exchange of reagents and buffer.

FIG. 5 is a schematic representation of a reaction center array. The left side panel (Microscope Field) depicts the view of an entire array as recorded by four successive detection events (one for each of the separate fluorochromes). The center panel depicts a magnified view of a part of the field showing the spacing of individual reaction centers. The far right panel depicts the camera's view of a single reaction center.

FIG. 6 is a schematic representation of the principle of the evanescent wave.

FIG. 7 is a schematic representation of a direct nucleic acid sequencing set up using total internal reflection fluorescence microscopy.

FIG. 8 is a schematic representation of an example of a data acquisition algorithm obtained from a 3×3 matrix.

DETAILED DESCRIPTION OF THE INVENTION

The present invention provides a novel sequencing apparatus and a novel sequencing method. The method of the present invention, referred to herein as Direct Nucleic Acid Sequencing (DNAS), offers a rapid, cost effective, high throughput method by which nucleic acid molecules from any source can be readily sequenced without the need for prior amplification. DNAS can be used to determine the nucleotide sequence of numerous single nucleic acid molecules in parallel.

1. DNAS Reaction Center Array

Polymerases are attached to the solid support, spaced at regular intervals, in an array of reaction centers, present at a periodicity greater than the optical resolving power of the microscope system. Preferably, only one polymerase molecule is present in each reaction center, and each reaction center is located at an optically resolvable distance from the other reaction centers. Sequencing reactions preferably occur in a thin aqueous reaction chamber comprising a sealed cover slip and an optically transparent solid support.

Immobilization of polymerase molecules for use in nucleic acid sequencing has been disclosed by Densham in PCT application WO 99/05315. Densham describes the attachment of selected amino groups within the polymerase to a dextran or N-hydroxysuccinimide ester-activated surface. WO 99/05315; EP-A-0589867; Löfas et al., *Biosens. Bzoelectron* 10: 813-822 (1995). These techniques can be modified in the present invention to insure that the activated area is small enough so that steric hindrance will prevent the attachment of more than one polymerase at any given spot in the array.

The array of reaction centers containing a single polymerase molecule is constructed using lithographic techniques commonly used in the construction of electronic integrated circuits. This methodology has been used in the art to construct microscopic arrays of oilgodeoxynucleotides and arrays of single protein motors. See, e.g., Chee et al., Science 274: 610-614 (1996); Fodor et al., *Nature* 364: 555-556 (1993); Fodor et al., *Science* 251: 767-773 (1991); Gushin, et al., *Anal. Biochem.* 250: 203-211 (1997); Kinosita et al., *Cell* 93: 21-24 (1998); Kato-Yamada et al., *J. Biol. Chem.* 273: 19375-19377 (1998); and Yasuda et al., *Cell* 93: 1117-1124 (1998). Using techniques such as photolithography and/or electron beam lithography [Rai-Choudhury, *Handbook of Microlithography, Micromachining, and Microfabrication. Volume I. Microlithography*, Volume PM39, SPIE Press (1997); Service, *Science* 283: 27-28 (1999)], the substrate is sensitized with a linking group that allows attachment of a single modified protein. Alternatively, an array of sensitized sites can be generated using thin-film technology such as Langmuir-Blodgett. See, e.g., Zasadzinski et al., *Science* 263: 1726-1733 (1994).

The regular spacing of proteins is achieved by attachment of the protein to these sensitized sites on the substrate. Polymerases containing the appropriate tag are incubated with the sensitized substrate so that a single polymerase molecule attaches at each sensitized site. The attachment of the polymerase can be achieved via a covalent or non-covalent interaction Examples of such linkages common in the art include $Ni^{2+}$/hexahistidine, streptavidin/biotin, avidin/biotin, glutathione S-transferase (GST)/glutathione, monoclonal antibody/antigen, and maltose binding protein/maltose.

A schematic representation of a reaction center is presented in FIG. 3. A DNA polymerase (e.g., from *Thermus aquaticus*) is attached to a glass microscope slide. Attachment is mediated by a hexahistidine tag on the polymerase, bound by strong non-covalent interaction to a $Ni^{2+}$ atom, which is, in turn, held to the glass by nitrilotriacetic acid and a linker molecule. The nitrilotriacetic acid is covalently linked to the glass by a linker attached by silane chemistry. The silane chemistry is limited to small diameter spots etched at evenly spaced intervals on the glass by electron beam lithography or photolithography. In addition to the attached polymerase, the reaction center includes the template DNA molecule and an oligonucleotide primer both bound to the polymerase. The glass slide constitutes the lower slide of the DNAS reaction chamber.

Housing the array of DNAS reaction centers and mediating the exchange of reagents and buffer is the reaction chamber assembly. An example of DNAS reaction chamber assembly is illustrated in FIG. 4. The reaction chamber is a sealed compartment with transparent upper and lower slides. The slides are held in place by a metal or plastic housing, which may be assembled and disassembled to allow replacement of the slides. There are two ports that allow access to the chamber. One port allows the input of buffer (and reagents) and the other port allows buffer (and reaction products) to be withdrawn from the chamber. The lower slide carries the reaction center array. In addition, a prism is attached to the lower slide to direct laser light into the lower slide at such angle as to produce total internal reflection of the laser light within the lower slide. This arrangement allows an evanescent wave to be generated over the reaction center array. A high numerical aperture objective lens is used to focus the image of the reaction center array onto the digital camera system. The reaction chamber housing can be fitted with heating and cooling elements, such as a Peltier device, to regulate the temperature of the reactions.

By fixing the site of nucleotide incorporation within the optical system, sequence information can be obtained from many distinct nucleic acid molecules simultaneously. A diagram of the DNAS reaction center array is given in FIG. 5. As described above, each reaction center is attached to the lower slide of the reaction chamber. Depicted in the left side panel (Microscope Field) is the view of an entire array as recorded by four successive detection events (one for each of the separate fluorochromes). The center panel is a magnified view of a part of the field showing the spacing of individual reaction centers. Finally, the far right panel depicts the camera's view of a single reaction center. Each reaction center is assigned 100 pixels to ensure that it is truly isolated. The imaging area of a single pixel relative to the 1 µm×1 µm area allotted to each reaction center is shown. The density of reaction centers is limited by the optical resolution of the microscope system. Practically, this means that reaction centers must be separated by at least 0.2 µm to be detected as distinct sites.

2. Enzyme Selection

In general, any macromolecule which catalyzes formation of a polynucleotide sequence can be used as the polymerase. In some embodiments, the polymerase can be an enzymatic complex that: I) promotes the association (e.g., by hydrogen bonding or base-pairing) of a tag (e.g., a normal or modified nucleotide, or any compound capable of specific association with complementary template nucleotides) with the complementary template nucleotide in the active site; 2) catalyzes the formation a covalent linkage between the tag and the synthetic strand or primer; and 3) translates the active site to the next template nucleotide.

While the polymerases will typically be proteinaceous enzymes, it will be obvious to one of average skill in the art that the polymerase activity need not be associated with a proteinaceous enzyme. For example, the polymerase may be a nucleic acid itself, as in the case of ribozymes or DNA-based enzymes.

A large selection of proteinaceous enzymes is available for use in the present invention. For example, the polymerase can be an enzyme such as a DNA-directed DNA polymerase, an RNA-directed DNA polymerase a DNA-directed RNA polymerase or and RNA-directed RNA polymerase. Some polymerases are multi-subunit replication systems made up of a core enzyme and associated factors that enhance the activity of the core (e.g., they increase processivity or fidelity of the core subunit). The enzyme must be modified in order to link it to the support. The enzyme can be cloned by techniques well known in the art, to produce a recombinant protein with a suitable linkage tag. In a preferred embodiment, this linkage is a hexahistidine tag, which permits strong binding to nickel ions on the solid support. Preferred enzymes are highly processive, i.e., they remain associated with the template nucleotide sequence for a succession of nucleotide additions, and are able to maintain a polymerase-polynucleotide complex even when not actively synthesizing. Additionally, preferred polymerases are capable of incorporating 3'-modified nucleotides. Sufficient quantities of an enzyme are obtained using standard recombinant techniques known in the art. See, for example. Dabrowski and Kur. *Protein Expr. Purif.* 14: 131-138 (1998).

2.1 DNA Polymerase

In a preferred embodiment, sequencing is done with a DNA-dependent DNA polymerase DNA-dependent DNA polymerases catalyze the polymerization of deoxynucleotides to form the complementary strand of a primed DNA template. Examples of DNA-dependent DNA polymerases include, but are not limited to, the DNA polymerase from *Bacillus stearothermophilus* (Bst), the *E. coli* DNA polymerase I Klenow fragment, *E. coli* DNA polymerase III holoenzyme, the bacteriophage T4 and T7 DNA polymerases, and those from *Thermus aquaticus* (Taq), *Pyrococcus furiosis* (Pfu), and *Thermococcus litoralis* (Vent). The polymerase from T7 gene 5 can also be used when complexed to thioredoxin. Tabor et al., *J. biol. Chem.*, 262: 1612-1623 (1987). The Bst DNA polymerase is preferred because it has been shown to efficiently incorporate 3'-O-(-2-Nitrobenzyl)-dATP into a growing DNA chain, is highly processive, very stable, and lacks 3'-5 exonuclease activity. The coding sequence of this enzyme has been determined. See U.S. Pat. Nos. 5,830,714 and 5,814,506, incorporated herein by reference.

In an alternative preferred embodiment where RNA is used as template, the selected DNA-dependent DNA polymerase functions as an RNA-dependent DNA polymerase, or reverse transcriptase. For example, the DNA polymerase from *Thermus thermophilus* (Tth) has been reported to function as an RNA-dependent DNA polymerase, or reverse transcriptase, under certain conditions. See, Meyers and Gelfand, *Biochem.* 30: 7661-7666 (1991). Thus, the Tth DNA polymerase is linked to the substrate and the sequencing reaction is conducted under conditions where this enzyme will sequence an RNA template, thereby producing a complementary DNA strand.

In some embodiments, a polymerase subunit or fragment is attached to the support, and other necessary subunits or fragments are added as part of a complex with the sample to be sequenced. This approach is useful for polymerase systems that involve a number of different replication factors. For example, to use the bacteriophage T4 replication system for DNAS sequencing, the gp43 polymerase can be attached to the support. Other replication factors, such as the clamp loader (gp44/62) and sliding clamp (gp45), can be added with the nucleic acid template in order to increase the processivity of the replication system. A similar approach can be used with *E. coli* polymerase III system, where the polymerase core is immobilized in the array and the β-dimer subunit (sliding clamp) and τ and γ subassembly (clamp loader) are added to the nucleic acid sample prior to DNAS sequencing. Additionally, this approach can be used with eukaryotic DNA polymerases (e.g., α or δ) and the corresponding PCNA (proliferating cell nuclear antigen). In some embodiments, the sliding clamp is the replication factor that is attached in the array and the polymerase moiety is added in conjunction with the nucleic acid sample.

2.2 Reverse Transcriptase

A reverse transcriptase is an RNA-dependent DNA polymerase—an enzyme that produces a DNA strand complementary to an RNA template. In an alternative preferred embodiment, a reverse transcriptase enzyme is attached to the support for use in sequencing RNA molecules. This permits the sequencing of RNAs taken directly from tissues, without prior reverse transcription. Examples of reverse transcriptases include, but are not limited to, reverse transcriptase from Avian Myeloblastosis Virus (AMV), Moloney Murine Leukemia Virus, and Human Immunodeficiency Virus-1 (HIV-1). HIV-1 reverse transcriptase is particularly preferred because it is well characterized both structurally and biochemically. See, e.g. Huang, et al., *Science* 282: 1669-1675 (1998).

In an alternative preferred embodiment, the immobilized reverse transcriptase functions as a DNA-dependent DNA polymerase, thereby producing a DNA copy of the sample or target DNA template strand.

2.3 RNA Polymerase

In yet another alternative preferred embodiment, a DNA-dependent RNA polymerase is attached to the support, and uses labeled-caged ribonucleotides to generate an RNA copy of the sample or target DNA strand being sequenced. Preferred examples of these enzymes include, but are not limited to, RNA polymerase from *E. coli* [Yin, et al., *Science* 270: 1653-1657 (1995)] and RNA polylmerases from the bacteriophages T7, T3, and SP6. In an alternative, preferred embodiment, a modified T7 RNA polymerase functions as a DNA dependent DNA polymerase. This RNA polymerase is attached to the support and uses labeled-caged deoxyribonucleotides to generate a DNA copy of a DNA template. See, e.g. Izawa, et al. *J. Biol. Chem.* 273: 14242-14246 (1998).

2.4 RNA Dependent RNA Polymerase

Many viruses employ RNA-dependent RNA polymerases in their life-cycles. In a preferred embodiment, an RNA-dependent RNA polymerase is attached to the support, and uses labeled-caged ribonucleotides to generate an RNA copy of a sample RNA strand being sequenced. Preferred examples of these enzymes include, but are not limited to. RNA-dependent RNA polymerases from the viral families: bromoviruses, tobamoviruses, tombusvirus, leviviruses, hepatitis C-like viruses, and picornaviruses. See, e.g., Huang et al., *Science* 282: 1668-1675 (1998); Lohmann et al., *J. Virol.* 71: 8416-8428 (1997); Lohmann et al., *Virology* 249:108-118 (1998), and O'Reilly and Kao, *Virology* 252: 287-303 (1998).

3. Sample Preparation

The nucleic acid to be sequenced can be obtained from any source. Example nucleic acid samples to be sequenced include double-stranded DNA, single-stranded DNA, DNA from plasmid, first strand cDNA, total genomic DNA, RNA, cut/end-modified DNA (e.g. with RNA polymerase promoter), in vitro transposon tagged (e.g., random insertion of RNA polymerase promoter). The target or sample nucleic acid to be sequenced is preferably sheared (or cut) to a certain size, and annealed with oligodeoxynucleotide primers using techniques well known in the art. Preferably, the sample nucleic acid is denatured, neutralized and precipitated and then diluted to an appropriate concentration, mixed with oligodeoxynucleotide primers, heated to 65° C. and then cooled to room temperature in a suitable buffer. The nucleic acid is then added to the reaction chamber after the polymerase has been immobilized on the support or, alternatively, is combined with the polymerase prior to the immobilization step.

3.1 In Vitro Transposon Tagging of Template DNA

In an alternative preferred embodiment purified transposases and transposable element tags will be used to randomly insert specific sequences into template double stranded DNA. In one configuration the transposable element contains the promoter for specific RNA polymerase. Alternatively, the inverted repeats of the transposable elements can be hybridized with complementary oligodeoxynucleotide primers for DNAS with DNA polymerases. Preferred examples of these transposases and transposable elements include, but are not limited to. TC1 and TC3A from *C. elegans* and the engineered teleost system Sleeping Beauty. See, e.g. Ivics et al. *Cell* 91:501-510 (1997); Plasterk, *Curr. Top. Microbiol. Immunol.* 204, 125-143 (1996); van Luenen et al. *EMBO J.* 12: 2513-2520 (1993), and Vos et al., *Genes Dev.* 10 755-761 (1996).

3.2 Double Stranded Template DNA

In yet another embodiment, double stranded DNA is sequenced by Bst DNA polymerase without the need for primer annealing. See, e.g. Lu et al. *Chin. J Biotechnol.* 8: 29-32 (1992).

3.3 Primers

Various primers and promoters are known in the art and may be suitable for sequence extension in DNAS. Examples include random primers, anchor point primer libraries, single-stranded binding protein masking/primer library, and primase.

In a preferred embodiment anchored primers are used instead of random primers. Anchor primers are oligonucleotide primers to previously identified sequences. Anchor primers can be used for rapid determination of specific sequences from whole genomic DNA, from cDNAs or RNAs. This will be of particular use for rapid genotyping, and/or for clinical screening to detect polymorphisms or mutations in previously identified disease-related genes or other genes of interest. Once genome projects, and other studies, have identified sequences of particular interest then oligonucleotides corresponding to various locations in and around that sequence can be designed for use in DNAS. This will maximize the quantity of useful data that can be obtained from a single sequencing run, particularly useful when complex DNA samples are used. For identification of mutated or polymorphic disease genes this technique will obviate the need to perform genotyping by any other means currently in use, including using single strand conformation polymorphism (SSCP) [Orita et al., *Genomics* 5: 874-879 (1989)]. PCR sequencing or DNA array hybridization technology [Hacia. *Nat. Genet.* 21: 42-47 (1999)]. Direct sequencing of disease gene is superior to SSCP and hybridization technologies because they are relatively insensitive and may frequently positively or negatively identify mutations. Many anchor oligonucleotides can be mixed together so that hundreds or thousands of genes or sequences can be identified simultaneously. In essence every known or potential disease-related gene can be sequenced simultaneously from a given sample.

4. Labeled-caged Terminating Nucleotides

To be useful as a chain terminating substrate for the methods of the present invention, a nucleotide must contain a detectable label that distinguishes it from the other three nucleotides Furthermore, the chain terminating, nucleotides must permit base incorporation, it must terminate elongation upon incorporation, and it must be capable of being uncaged to allow further chain elongation, thereby permitting repetitive cycles of incorporation, monitoring to identify incorporated bases, and uncaging to allow the next cycle of chain elongation. Uncaging of the nucleotides can be accomplished enzymatically, chemically, or preferably photolytically.

The basic molecule is an NTP with modification at the 3'-OH(R), the 2'-OH(R'), or the base (R"). In a standard dideoxy NTP, R=H, R'=H, and R"=H.

R=H, R'=OH, and R"=H is a chain terminator for RNA polymerases.

One set of useful chain-terminating nucleotides for the methods of the present invention is R=cage/label, R'=(H or OH), and R"=H. In a preferred embodiment, the modified nucleotide is a label (e.g., a fluorophore) linked to the sugar moiety by a 3'-O-(-2-Nitrobenzyl) group. The modified 3'-O-(-2-Nitrobenzyl)-dNTP is incorporated into the growing DNA chain by Bst DNA polymerase linked to a support. In order to resume chain elongation, the nucleotide is uncaged by removal of the 2-Nitrobenzyl group (with its corresponding detectable label) by exposure to light of the appropriate frequency. The modified nucleotide 3'-O-(-2-Nitrobenzyl)-dATP has previously been used in a single round of nucleotide incorporation and uncaging. Metzker et al., *Nucleic Acids Res.* 22: 4259-4267 (1994). See also Cheesman, U.S. Pat. No. 5,302,509, incorporated herein by reference.

An alternative set of useful chain-terminating nucleotides has the configuration R=cage. R'=(H or OH), and R"=cage/label. In a preferred embodiment, the detachable labeling group is a label (e.g., a fluorophore) linked to the base of the nucleotide by a 2-Nitrobenzyl group, and the detachable blocking group is a 3'-O-(-2-Nitrobenzyl) group. The modified nucleotide is incorporated into the growing DNA chain by Bst DNA polymerase linked to a support. In order to resume chain elongation, the nucleotide is uncaged by removal of both the labeling group and the blocking group by exposure to light of the appropriate frequency.

In either of these configurations it may prove advantageous to place two labels (e.g. two fluorochromes) on each cage, as has been described in WO 98/33939.

For sequencing when the synthetic strand is RNA, labeled-caged ribonucleotides (i.e. R'=OH) are synthesized as modified nucleotides designed for incorporation by support-linked RNA polymerase.

4.1 Fluorescent Labels

The use of fluorescent tags to identify nucleotides in nucleic acid sequencing is well known in the art. See, e.g., U.S. Pat. Nos. 4,811,218; 5,405,747; 5,547,839 and 5,821,058, each incorporated herein by reference. Metzker and Gibbs have recently disclosed a family of fluorescently tagged nucleotides based on the Cy fluorophores with improved spectral characteristics. U.S. Pat. No. 5,728,529, incorporated herein by reference. Alternative sets of fluorophores include: the rhodamine based fluorophores, TARAM, ROX, JOE, and FAM; the BigDye® fluorophores (Applied Biosystems, Inc.); and the BODIPY® fluorophores (U.S. Pat. No. 5,728,529).

In a preferred embodiment of the present invention, a fluorescent label is attached to the photolabile 3' blocking group (i.e., cage). Examples of modified nucleotides for DNAS are schematically illustrated in FIG. 1 (Panels A-C). Panel A depicts a deoxyadenosine triphosphate modified by attachment of a photolabile linker-fluorochrome conjugate to the 3' carbon of the ribose. Photolysis of the linker by <360 nm light causes the fluorochrome to dissociate, leaving the 3'-OH group of the nucleotide intact. Panel B depicts an alternative configuration in which the fluorochrome is attached to the base of the nucleotide by way of a photolabile linker. The 3'-OH is blocked by a separate photolabile group Modified nucleotides such as those depicted in Panels A and B are examples of labeled-caged deoxyribonucleotides for use in DNAS. A variety of fluorochromes and photolabile groups can be used in the synthesis of labeled-caged deoxyribonucleotides. Additionally, ribonucleotides can also be synthesized for use with RNA polymerases. Four fluorochromes with distinct spectral properties allow the four nucleotides to be distinguished during the detection phase of the DNAS reaction cycle. FIG. 1 (Panel C) provides a schematic representation of four different labeled-caged terminator nucleotides for use in direct nucleic acid sequencing.

After incorporation of the labeled-caged terminator nucleotides by the immobilized polymerase molecules, the fluorophores are illuminated to excite fluorescence in each of the four species of fluorophore. The emission at each point in the array is optically detected and recorded. Once the sequence information has been obtained, the photolabile linkers are removed by illumination with light at the uncaging wavelength (<360 nm)

Depicted in FIG. 2 is a single round of the reaction cycle. i.e., (1) the incorporation of a labeled-caged nucleotide; (2) the detection of the labeled nucleotide; and (3) the unblocking of the caged nucleotide. It is through successive rounds of the DNAS reaction cycle that primary sequence information is deduced. In the first panel (Step 1) is an example single stranded template DNA (3'-AGCAGTCAG-5') on the left side is a short primer sequence (5'-TC-3') and a labeled-caged dGTP undergoing incorporation. In the middle panel (Step 2) the fluorochrome, BODIPY$^{564}/_{570}$, is excited by YAG laser illumination at 532 nm. The fluorochrome emits light centered at a wavelength of 570 nm, which is detected by the microscope system. Finally, in Step 3, photolysis of the linker by illumination with <360 nm light simultaneously dissociates fluorochrome label and releases the 3' block. As a result the primer is extended by one base (5'-TCG-3') and the 3'-OH is restored so that another nucleotide can be incorporated on the next cycle.

4.2 Quantum Dot Labels

In an alternative preferred embodiment of the present invention, each of the caged terminators is labeled with a different type of quantum dot. Recently, highly luminescent semiconductor quantum dots (QDs) have been covalently coupled to biomolecules. Chan and Nie. *Science* 281: 2016-2018 (1998). These luminescent labels exhibit improved spectral characteristics over traditional organic dyes, and have been shown to allow sensitive detection with a confocal fluorescence microscope at the single dot level. In this embodiment, the caged quantum dot terminators are incorporated, detected, and uncaged in a manner similar to that described above for the fluorescent caged terminators.

4.3 Plasmon Resonance Particles

In a preferred embodiment, each of the caged terminators is labeled with a colloidal silver plasmon-resonant particle (PRP). Schultz et al., *J. Clin. Ligand Assay* 22: 214-216 (1999); Schultz et al., *Proc. Natl. Acad. Sci.* 97: 996-1001 (2000). PRPs are metallic nanoparticles, typically 40-100 nm in diameter which can be engineered to efficiently scatter light anywhere in the visible range of the spectrum. These particles are bright enough to be used for single molecule detection. PRPs were shown to produce a scattering flux equivalent to that from 5 million fluorescein molecules, and more than 105-fold greater than that from typical quantum dots. Schultz et al. *Proc. Natl. Acad. Sci.* 97: 996-1001 (2000). Furthermore, when imaged by a standard CCD, the spatial peak can be located to a precision of 10 Å, similar precision to that observed with imaging single fluorophores on gold nanoparticles. Denk and Webb, *Appl. Opt.* 29: 2382-2391 (1990). To facilitate detection, in certain embodiments, each different type of nucleotide is modified with a PRP of a different color. In order to resolve the signal from two PRPs incorporated into a sample at neighboring reaction centers, the reaction centers must at least be separated by a coherence length (approximately the wavelength of the illuminating light). Additionally, Raman scattering may be used to detect the PRPs. Nie and Emory, *Science* 275: 1102-1106 (1997).

5. Detection of Incorporated Nucleotides

Advances in microscopic techniques have allowed the spectroscopic detection of single molecules. See, Nie and Zare, *Annu. Rev. Biophys. Biomol. Struct.* 26: 567-596 (1997), and Keller et al., *Appl. Spectrosc.* 50: 12A-32A (1996). For example, single fluorescent molecules in aqueous solution can be visualized under total internal reflection fluorescence microscopy (TIRFM), confocal microscopy, fluorescence resonance energy transfer (FRET), or surface plasmon resonance spectroscopy (SPR). See, Dickson et al., *Nature* 388: 355-358 (1997); Dickson et al., *Science* 274: 966-969 (1996); Ishijima et al., *Cell* 92: 161-171 (1998); Iwane et al., *FEBS Lett.* 407: 235-238 (1997); Nie et al., *Science* 266: 1018-1021 (1994); Pierce et al., *Nature* 388: 338 (1997); Ha et al., *Proc. Natl. Acad. Sci. USA* 93: 6264-6268 (1996), and Gordon et al., *Biophys. J.* 74: 2702-2713 (1998). Yokota et al., *Phys. Rev. Letts.* 80:4606-4609 (1998). Since single molecules can be detected spectroscopically, cloned nucleic acid samples are no longer necessary for sequencing. A single copy of template, contained within a reaction center is a sufficient sample size. The apparatus and methods of the present invention allow the resolution of signals from single nucleotide tags within an optical plane and their subsequent conversion into digital information. Photons are collected from a thin plane roughly equivalent to the volume within which the enzyme and newly synthesized base reside.

5.1 TIRFM

When light is directed at a particular angle into a refractive medium of set width, such as a glass slide, total internal reflection (TIR) will result. Above the plane of the refractive medium an electromagnetic phenomenon known as an evanescent wave occurs. The principle of the evanescent wave is depicted in FIG. 6. The evanescent wave extends from the surface to a distance of the order of the wavelength of light. Importantly, an evanescent wave can be used to excite fluorochromes within this distance When this phenomenon is used for microscopy it is called total internal reflection fluorescence microscopy (TIRFM) The arrangement of microscope slides, prism and laser beam depicted in this figure will lead to TIR within the lower slide and thus an evanescent wave will be generated within ~150 n of the upper surface of the lower slide. Fluorochrome molecules, such as those within DNAS reaction centers, will be excited and can be detected optically using the objective lens, microscope and camera system. A high signal-to-noise ratio is achieved using evanescent wave excitation because only those fluorochrome molecules within the evanescent wave are stimulated.

In a preferred embodiment TIRFM is used for detection. Depicted in FIG. 7 is the arrangement of equipment required to carry out DNAS using TIRFM. A standard laboratory microscope stand houses the reaction chamber assembly, objective lens, filter wheel, microchannel plate intensifier, and cooled CCD camera. Laser light is directed into the prism by dichroic mirrors and computer controlled shutters. Evanescent wave excitation is used to stimulate the sample. Evanescent wave excitation is achieved by total internal reflection at the glass-liquid interface. At this interface, the optical electromagnetic field does not abruptly drop to zero, but decays exponentially into the liquid phase. The rapidly decaying field (evanescent wave) can be used to excite fluorescent molecules in a thin layer of approximately 150 nm immediately next to this interface. See, PCT Patent Application WO 98/33939, incorporated herein by reference. The sensitivity that allows single molecule detection arises from the small sample volume probed. One advantage of TIRFM is that the entire reaction center array can be imaged simultaneously. Images of the reaction center array are focused onto the face of the microchannel plate intensifier through barrier filters carried on the filter wheel. The microchannel plate intensifier amplifies the image and transfers it to the face of the cooled CCD camera. Image data are read from the CCD chip and processed on a microcomputer. A stimulating laser, or set of stimulating lasers, is directed to the specimen by way of an optical table. Another laser uncages the 3'-OH protecting group. Additional lasers may be required for optimal fluorochrome stimulation. A filter wheel is also included in the invention to change barrier filters so that the four different fluorochromes (each corresponding to a different type of labeled-caged nucleotide) are unambiguously distinguished.

As shown in FIG. 7, a prism is built onto the microscope slide to direct the laser into the slide from outside the microscope. Ishijima et al., *Cell* 92: 161-171 (1998). Alternatively, objective-type TIRFM can be used for fluorescence detection. Laser light is directed through an objective lens off-center such that the critical angle is achieved using the objective lens itself. See, Tokunaga et al. *Biochem. Biophys. Res. Comm.* 235: 47-53 (1997).

5.2 Confocal Microscopy

In an alternative preferred embodiment, confocal microscopy is used for detection. In confocal microscopy, a laser beam is brought to its diffraction-limited focus inside a sample using an oil immersion, high numerical-aperture (NA) objective lens. Single molecules have been detected in solution by multi-photon confocal fluorescence. Mertz, et al., *Opt. Lett.* 20:2532-2534 (1995). In one embodiment of this invention, the nucleotide labels are detected by scanning multi-photon confocal microscopy. Nie et al. *Science* 266: 1018-1021 (1994).

5.3 Fluorescence Resonance Energy Transfer (FRET)

In an alternative preferred embodiment, FRET technology is used for detection. Fluorescence resonance energy transfer is a distance-dependent interaction between the electronic excited states of two dye molecules in which excitation is transferred from a donor molecule to an acceptor molecule without emission of a photon. FRET is dependent on the inverse sixth power of the intermolecular separation, making it useful over distances comparable with the dimensions of biological macromolecules. Thus, FRET is an important technique for investigating a variety of biological phenomena that produce changes in molecular proximity.

This technique makes use of some unusual properties of dye molecules. In experiments that use fluorescent dyes, the dye molecule is typically excited at one wavelength of light and data is collected at a longer wavelength. However, when two different dye molecules are placed very close together, light can be absorbed by one molecule (the donor), and its emission can then be immediately captured by the adjacent molecule (the acceptor). Light at a still longer wavelength is then emitted from the acceptor. In most applications, the donor and acceptor dyes are different, in which case FRET can be detected by the appearance of sensitized fluorescence of the acceptor or by quenching of donor fluorescence. When the donor and acceptor are the same, FRET can be detected by the resulting fluorescence depolarization. Donor and acceptor molecules must be in close proximity (typically 10-100 Å). Absorption spectrum of the acceptor must overlap fluorescence emission spectrum of the donor, and donor and acceptor transition dipole orientations must be approximately parallel.

FRET can be employed to increase signal to noise ratios. Additionally, FRET can be used in DNAS to avoid the need for a photolabile linker on the fluorochromes. FRET is commonly used to measure the distance between molecules or parts of them, or to detect transient molecular interactions. In practice candidate molecules, or different parts of the same molecule, are modified with two different fluorescent groups. The solution is then excited by light corresponding to the shorter excitation wavelength of the two fluorochromes. When the second fluorochrome is in close proximity to the first, it will be excited by the emitted energy of the former and emit at its own characteristic wavelength. The efficiency (quantum yield) of the conversion is directly related to the physical distance between the two fluorochromes. For specific application to DNAS, polymerase molecules are tagged with a fluorochrome that behaves as a photon donor for the modified nucleotides. This would limit their excitation to the active site of the polymerase or any other appropriate part of the polymerase. Such an arrangement would significantly increase the signal-to-noise ratio of nucleotide detection. Moreover, because only nucleotides within the polymerase are excitable FRET as applied to DNAS would render unnecessary the removal of previously incorporated fluorescent moieties. FRET has been performed at the single molecule level as required for DNAS [Ha et al., *Proc Natl. Acad. Sci. USA* 93: 6264-6268 (1996)], and has been optimized for quantification in fluorescence microscopy. Gordon et al., *Biophys. J.* 74: 2702-2713 (1998). Optimally the polymerase would be synthesized as a recombinant green fluorescent protein (GFP) fusion protein as this would eliminate the need to derivatize the polymerase and unlike most commonly used fluorochromes GFP is substantially resistant to photobleaching. However, we may find that the optimal arrangement is a chemically modified polymerase to which a synthetic fluorochrome or quantum dot has been attached.

5.4 Surface Plasmon Resonance

In one embodiment, surface plasmon resonance (SPR) spectroscopy is used to detect the incorporation of label into the nucleic acid sample. SPR is used to measure the properties of a solution by detecting the differences in refractive index between the bulk phase of the solution and the evanescent wave region. SPR has been recently used to for single molecule imaging of fluorescently labeled proteins on metal by surface plasmons in aqueous solution. Yokota et al., *Phys. Rev. Letts.* 80:4606-4609 (1998). This technique involves coating the reaction chamber surface with a thin layer of metal in order to enhance the signal from fluorescently labeled nucleotides.

5.5 The DNAS Detector

The detector is a cooled CCD camera fitted with a microchannel plate intensifier. A block diagram of the instrument set-up is presented in FIG. 7. Recently available intensified-cooled CCD cameras have resolutions of at least 1000×1000 pixels. In a preferred embodiment of this invention, an array consists of 100×100 reaction centers. Thus, when the array is imaged onto the face of the camera, each reaction center is allotted approximately 10×10 pixels. DNAS uses a 63×1.4 NA lens to image an array (100×100 µm grid) of regularly spaced reaction centers, depicted in FIG. 5. Information can be simultaneously recorded from 10,000 reaction centers. This expected resolution is comparable to that achieved in a recent report, whereby TIRFM was used to image a sample of nile red fluorophores, and produced images of a large number of single molecules. A single nile red molecule was unambiguously imaged in an 8×8 pixel square. Dickson et al., *Nature* 388: 355-358 (1997).

6. The Sequencing Cycle

Housing the array of DNAS reaction centers and mediating the exchange of reagents and buffer is the reaction chamber assembly. The reaction chamber is a sealed compartment with transparent upper and lower slides. The slides are held in place by a metal or plastic housing, which may be assembled and disassembled to allow replacement of the slides. There are two ports that allow access to the chamber.

One port allows the input of buffer (and reagents) and the other port allows buffer (and reaction products) to be withdrawn from the chamber. The lower slide carries the reaction center array. In addition, a prism is attached to the lower slide to direct laser light into the lower slide at such angle as to produce total internal reflection of the laser light within the lower slide. This arrangement allows an evanescent wave to be generated over the reaction center array. A high numerical aperture objective lens is used to focus the image of the reaction center array onto the digital camera system. The reaction chamber housing can be fitted with heating and cooling elements, such as a Peltier device, to regulate the temperature of the reactions. A nucleic acid sample is introduced to the reaction chamber in buffered solution containing all four labeled nucleoside triphosphate terminators.

A schematic representation of the reaction chamber assembly is presented in FIG. 4. Reaction centers are monitored by the microscope system until a majority of reaction centers contain immobilized polymerase bound to the template with a single incorporated labeled-caged terminator nucleotide. The reaction chamber is then flushed with a wash buffer. Specific nucleotide incorporation is then determined for each reaction center. Following detection, the reaction chamber is irradiated to uncage the incorporated nucleotide and flushed with wash buffer once again. The presence of labeled nucleotides is once again monitored before fresh reagents are added to reinitiate synthesis. This second detection verifies that a reaction center is successfully uncaged. The presence of a labeled nucleotide in the chamber during this step indicates that the reaction center has not been uncaged. Accordingly, the subsequent reading from this reaction center during the next detection step of the cycle will be ignored. Thus, by ignoring the signals from reaction centers that are not successfully uncaged, the methods of the present invention avoid the problems caused by incomplete uncaging in sequencing methods of the prior art. The sequencing cycle outlined above is repeated until a large proportion of reaction centers persistently fail to incorporate or uncage additional nucleotides.

Methods for regulating the supply (and removal) of reagents to the reaction centers, as well as the environment of the reaction chamber (e.g., the temperature, and oxidative environment) are incorporated into the reaction chamber using techniques common in the art. Examples of this technology are outlined in: Kricka, Clinical Chem. 44: 2008-2014 (1998); see also U.S. Pat. No. 5,846,727.

7. Sequence Acquisition Software

The sequence acquisition software acquires and analyzes image data during the sequencing cycle. At the beginning of a sequencing experiment, a bin of pixels containing each reaction center is determined. During each sequencing cycle, four images of the entire array are produced, and each image corresponds to excitation of one of the four fluorescently labeled nucleotide bases A, C, G, or T (U). For each reaction center bin, all of the four images are analyzed to determine which nucleotide species has been incorporated at that reaction center during that cycle. As described above, the reaction center bin corresponding to a certain reaction center contains a 10×10 array of pixels. The total number of photons produced by the single fluorophore in that reaction center is determined by the summation of each pixel value in the array. Typically, 500-1500 photons are emitted from a single fluorophore when excited for 100 milliseconds with a laser producing an intensity of 5 kW/cm² at the surface of the microscope slide. Dickson et al., *Science* 274: 966-969 (1996). The sums of the reaction center bins from each of the four images are compared, and the image that produces a significant sum corresponds to the newly incorporated base at that reaction center. The images are processed for each of the reaction centers and an array of incorporated nucleotides is recorded. An example of a data acquisition algorithm is provided in FIG. 8. Such processing is done in real time at low cost with modern image processing computers.

Multiple reads of the reaction center array may be necessary during the detection step to ensure that the four nucleotides are properly distinguished. Exposure times can be as low as 100 msec. and the readout time of the CCD chip can be as long as 250 msec. Thus, the maximum time needed for four complete reads of the array is 1.5 seconds. The total time for a given cycle, including reagent addition, removal, and washes, is certainly less than 10 seconds. Accordingly, a sequencing apparatus consisting of an array of 10,000 reaction centers is able to detect at least 360 bases per site per hour, or 3.6 Megabases per hour of total sequence, as a conservative estimate. This rate is significantly faster than those of traditional sequencing methodologies.

In addition to short sequencing times, the methods of the present invention do not require the time-consuming processes of sample amplification (cloning, or PCR), and gel electrophoresis. The lack of consumables necessary for sample amplification and electrophoresis, coupled with small reagent volumes (the reaction chamber volume is on the order of 10 microliters) and reduced manual labor requirements drastically reduce the cost per nucleotide sequenced relative to traditional sequencing techniques.

8. Sequence Analysis Software

Depicted in FIG. 8 is an example of DNAS data acquisition using a 3×3 array of reaction centers. In a typical configuration, however, DNAS would utilize an array of 100×100 reaction centers. In this example, four cycles of DNAS are presented. For each cycle, four images of the array are produced. Each image corresponds to a specific excitation wavelength and barrier filter combination, and thus corresponds to the incorporation of a specific modified nucleotide. Consider the upper left array (Cycle 1, A). In this case when using the BODIPY set of modified nucleotides 'A' is 3'-O-(DMNPE-(BODIPY$^{493}/_{503}$))-2' deoxy ATP. Thus the reaction center array is illuminated with 488 nm light from the Ar laser and the image focused through a 503 nm barrier filter. Each of the nine elements in the 3×3 matrix corresponds to a 10×10 pixel area of the CCD camera output. For each of the four images each reaction center pixel group is analyzed to determine whether a the given nucleotide has been incorporated. Thus we see in the example that in Cycle 1, A, modified deoxyATPs were incorporated at reaction centers X1 and Z1. Hence, in the table the first nucleotides recorded for reaction centers X1 and Z1 are 'A's. If we consider a given reaction center, e.g. reaction center X1, over the four cycles of DNAS we see that in the first cycle the reaction center has incorporated a 'A', in the second cycle a 'C', in the third cycle a 'C' and in the fourth cycle an 'T'. Hence the sequence fragment of the template DNA bound at reaction center Y3 is the reverse complement of 5'-ACCT-3', which is 5'-TGGA-3'. The primary sequence exists as an array of sequences, each derived from a single reaction center. The length of each reaction center sequence will depend upon the number of cycles a given center remains active in an experiment. Based on the processivity of cloned polymerases reported in the art, sequence lengths of several hundred to several thousand bases are expected.

In one embodiment of the present invention, a nucleic acid sample is sheared prior to inclusion in a reaction center. Once these fragments have been sequenced, sequence analysis software is used to assemble their sequences into contiguous stretches. Many algorithms exist in the art that can compare sequences and deduce their correct overlap. New algorithms have recently been designed to process large amounts of sequence data from shotgun (random) sequencing approaches.

In one preferred embodiment, an algorithm initially reduces the amount of data to be processed by using only two smaller sequences derived from either end of the sequence deduced from a single reaction center in a given experiment. This approach has been proposed for use in shotgun sequencing of the human genome. Rawlinson, et al., *J. Virol* 70: 8833-8849 (1996); Venter et al., *Science* 280: 1540-1542 (1998). It employs algorithms developed at the Institute for Genome Research (TIGR). Sutton, et al., *Genome Sci. Technol.* 1: 9 (1995).

In an alternative preferred embodiment, raw data is compressed into a fingerprint of smaller words (e.g., hexanucleotide restriction enzyme sites) and these fingerprints can be compared and assembled into larger continuous blocks of sequence (contigs). This technique is similar to that used to deduce overlapping sequences after oligonucleotide hybridization. Idury and Waterman, *J. Comput. Biol.* 2: 291-306 (1995). Yet another embodiment uses existing sequence data, from genetic or physical linkage maps, to assist the assembly of new sequence data from whole genomes or large genomic pieces.

9. Utility of DNAS (a) Clinical Applications

The importance of genetic diagnoses in medicine cannot be understated. Most obvious is the use of techniques that can identify carriers of harmful genetic traits for pre-natal and neo-natal diagnosis. Currently, biochemical tests and karyotype analyses are the most commonly used techniques, but these have clear limitations. Biochemical tests are only useful when there is a change in the activity or levels of an enzyme or protein which has been associated with the disease state and for which a specific test has been determined. Even when a protein has been attributed to a disease state the development of such reagents can be difficult, expensive and time consuming. Karyotypic analyses are only useful for identifying gross genetic disorders such as ploidy, translocations and large deletions. Although it is theoretically possible to determine whether individuals possess defective alleles of a given gene by current DNA techniques, effective screening programs are only currently practicable in cases in which a common mutation is associated with the disease and its presence can be determined by non-sequencing techniques.

The methods of the present invention permit large amounts of DNA sequence data to be determined from an individual patient with little technical effort, and without the need to clone patient DNA or amplify specific sequences by PCR. Single molecules can be sequenced directly from a simple DNA preparation from the patient's blood, tissue samples or from amniotic fluid. Accordingly, DNAS can be used for clinical diagnosis of genetic disorders, traits or other features predictable from primary DNA sequence information, such as prenatal, neo-natal and post-natal diagnoses or detection of congenital disorders; pathological analysis of somatic disease caused by genetic recombination and/or mutation; identification of loss of heterozygosity, point mutations, or other genetic changes associated with cancer, or present in pre-cancerous states.

The methods of the present invention can also be used to identify disease-causing pathogens (e.g., viral, bacterial, fungal) by direct sequencing of affected tissues.

(b) Functional Gene Identification

Large scale genetic screens for genes involved in certain processes, for example during development, are now common and are applied to vertebrates with large genomes such as the zebrafish (*Damo rerio*) and the amphibian *Xenopus tropicalis*. Attempts to clone mutant genes in mouse and human have been lengthy and difficult and even in more genetically, amenable organisms like zebrafish it is still time consuming and difficult.

Since the methods of the present invention permit the sequencing of an entire genome the size of a mammal in a short period of time, identification of mutant genes can be achieved by bulk sequence screening, i.e., sequencing whole genomes or large genomic segments of a carrier, and comparing to the sequence of whole genomes or large genomic segments of different members of a given species.

Similarly, the methods of the present invention allow facile sequencing of entire bacterial genomes. Sequence information generated in this fashion can be used for rapid identification of genes encoding novel enzymes from a wide variety of organisms, including extremophillic bacteria.

In addition, the methods of the present invention can also be used for assessment of mutation rates in response to mutagens and radiation in any tissue or cell type. This technique is useful for optimization of protocols for future mutation screens.

(c) Analysis of Genetic Alterations in Tumors

Many cancers, possibly all cancers, begin with specific alterations in the genome of a cell or a few cells, which then grow unchecked by the controls of normal growth. Much of the treatment of cancers is dependent upon the specific physiological response of these abnormal cells to particular agents.

The method of the present invention will allow the rapid generation of a genetic profile from individual tumors, allowing researchers to follow precisely what genetic changes accompany various stages of tumor progression. This information will also permit the design of specific agents to target cancer cells for tailor-made assaults on individual tumors.

(d) Analysis of Genetic Variation

Many important physiological traits, such as control of blood pressure, are controlled by a multiplicity of genetic loci. Currently, these traits are analyzed by quantitative trait linkage (QTL) analysis. Generally, in QTL analysis a set of polymorphic genetic linkage markers is utilized on a group of subjects with a particular trait, such as familial chronic high blood pressure. Through an analysis of the linkage of the markers with the trait, a correlation is drawn between a set of particular loci and the trait. Usually a handful of loci contribute the majority of the trait and a larger group of loci will have minor effects on the trait.

The methods of the present invention permit rapid whole genome sequencing. Thus, using the methods of the present invention, QTL analysis is executed at a very fine scale and, with a large group of subjects, all of the major loci contributing to a given trait and most of the minor loci are easily identified.

Moreover, the method of the present invention can be used for constructing phylogenetic trees and/or kinship relationships by estimation of previous genomic recombinations (e.g. inversion, translocation, deletion, point mutation), or by previous meiotic recombination events affecting the distribution of polymorphic markers. The method of the present invention can be used to identify mutations or polymorphisms, with the aim of associating genotype with phenotype. The method of the present invention can also be use to identify the sequence of those mutant or polymorphic genes resulting in a specific phenotype, or contributing to a polygenic trait.

(e) Agricultural Applications

Agricultural efficiency and productivity is increased by generating breeds of plants and animals with optimal genetic characteristics. The methods of the present invention can be used, for example, to reveal genetic variation underlying both desirable and undesirable traits in agriculturally important plants and animals. Additionally, the methods of the present invention can be used to identify plant and animal pathogens, and designing methods of combating them.

(f) Forensic Applications

The methods of the present invention can be used in criminal and forensic investigations, or for the purpose of paternity/maternity determination by genetically identifying samples of blood, hair, skin and other tissues to unambiguously establish a link between a suspected individual and forensically relevant samples. The results obtained will be analogous to results obtained with current genetic fingerprinting techniques, but will provide far more detailed information and will be less likely to provide false positive identification. Moreover, the identity of individuals from a mixed sample can be determined.

(g) Research Applications

The methods of the present invention can be used for several research applications, such as the sequencing of artificial DNA constructs to confirm/elicit their primary sequence, and/or to isolate specific mutant clones from random mutagenesis screens, the sequencing of cDNA from single cells, whole tissues or organisms from any developmental stage or environmental circumstance in order to determine the gene expression profile from that specimen; the sequencing of PCR products and/or cloned DNA fragments of any size isolated from any source.

The methods of the present invention can be also used for the sequencing of DNA fragments generated by analytical techniques that probe higher order DNA structure by their differential sensitivity to enzymes, radiation or chemical treatment (e.g., partial DNase treatment of chromatin), or for the determination of the methylation status of DNA by comparing sequence generated from a given tissue with or without prior treatment with chemicals that convert methylcytosine to thymine (or other nucleotide) as the effective base recognized by the polymerase. Further, the methods of the present invention can be used to assay cellular physiology changes occurring during development or senescence at the level of primary sequence.

The methods of the present invention can also be used for the sequencing of whole genomes or large genomic segments of transformed cells to select individuals with the desired integration status. For example, DNAS can be used for the screening of transfected embryonic stem cell lines for correct integration of specific constructs, or for the screening of organisms such as *Drosophila*, zebrafish, mouse, or human tissues for specific integration events.

Additionally, the method of the present invention can be used to identify novel genes through the identification of conserved blocks of sequence or motifs from evolutionarily divergent organisms. The method of the present invention can also be used for identification of other genetic elements (e.g., regulatory sequences and protein binding sites) by sequence conservation and relative genetic location.

The details of one or more embodiments of the invention have been set forth in the accompanying description above. Although any methods and materials similar or equivalent to those described herein can be used in the practice or testing of the present invention the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLE 1

Reaction Chamber Substratum Preparation, Nickel/chelator Conjugate

The fundamental unit of the DNAS methodology is the reaction center (FIG. 3). The reaction center comprises a polymerase molecule bound to a template nucleic acid molecule, and tethered to a fixed location on a transparent substrate via a high affinity interaction between groups attached to the polymerase and substrate respectively. In one configuration, DNAS reactions occur in a reaction chamber whose base, the substrate, is made of glass ($SiO_2$) modified so that polymerase molecules can be attached in a regular array. Using electron beam lithography a square array of dimensions 100 µm×100 µm is generated. Rai-Choudhury, *Handbook of Microlithography, Micromachining, and Microfabrication, Volume I; Microlithography*, Volume PM39, SPIE Press (1997). A small spot, <50 nm in diameter, is etched at every 1 µm interval in resist material covering the glass slide. This etching exposes the glass for subsequent derivatization in which a nitrilotriacetic acid group is covalently bound by way of silane chemistry. Schmid, et al., *Anal Chem* 69: 1979-1985 (1997). Each nitrilotriacetic acid group serves as a chelator for a $Ni^{2-}$ ion. The coordinated $Ni^{2-}$ ion can then be bound by hexahistidine moieties engineered into a variety of polymerase molecules. Thus an array of 10.000 polymerase molecules is generated in a 100 µm×100 µm array, which will be observed in an optical microscope system. In an alternative configuration biotin is covalently attached to each spot by way of silane chemistry. The biotin is then bound by streptavidin moieties covalently linked to, or engineered into, the polymerase molecules.

EXAMPLE 2

Microfluidic Reaction Chamber Allows Rapid Exchange of Reactants Buffer and Products The reaction chamber is a device that houses the array of reaction centers and regulates the environment. As described in Example 1, the substrate is a glass microscope slide prepared with a regular microscopic array of covalently moieties. A prism is attached to the slide on the surface opposite to the array. The prism directs laser light into the slide at such an angle that total-internal reflection of the laser light is achieved within the slide. Under this condition an evanescent wave is generated over the array during the sequencing reaction cycle. The slide and prism are fixed into an assembly, which will generate a sealed chamber with a volume of 1-10 µl (FIG. 4) Reagents and buffer are pumped into and outof the chamber through microfluidic ports on either side of the chamber. Complete exchanges of volume take place within 1 second and are mediated by electronically controlled valves and pumps.

EXAMPLE 3

Preparation of Labeled-Caged Chain Terminating Nucleotides

Preparation of Fluorochrome-Photolabile Linker Conjugate

Fluorochrome-liriked 2-nitrobenzyl derivatives are first generated as described by Anasawa, et al., WO 98/33939. Alternatively a sensitized photolabile linker (e.g., using DMNPE caging kit, Catalog Number D-2516, Molecular Probes, Inc.) may be first attached to the 3' group of the dNTP as detailed below and then linked to a fluorochrome using succinimide chemistry or otherwise. It may prove optimal to use a linker of variable length between the fluorochrome and the caging group to reduce possible steric hindrance caused by large chemical groups. Brandis, et al., *Biochemistry* 35: 2189-2200 (1996).

Preparation of 3'-O-modified-2'-deoxynucleotide analogs

3'-O-modified-2'-deoxynucleotides are synthesized by esterification of the 3'-OH group of dATP, dCTP, dGTP and dTTP. This is accomplished by several general methods. Metzker, et al., *Nucleic Acids Res* 22: 4259-4267 (1994).

Method 1:

First 2'-deoxy-5'-hydroxy-dNTPs are reacted with tert-butyldiphenylsilyl (TBDPS) in the presence of imidazole and dimethylformamide (DMF) producing 5'-protected deoxynucleotides. Then the resulting 2'-deoxy-5'-tert-1-butyldiphenylsilyl dNTP is dissolved in benzene and mixed with the halide derivative of the fluorochrome-photolabile linker conjugate in the presence of tetrabutylammonium hydroxide (TBAH) (and additionally NaOH in some cases) and stirred at 25° C. for 16 hours. The organic layer is extracted with ethyl acetate and washed with deionized water, saturated NaCl, dried over $Na_2SO_4$ and purified by flash chromatography using a stepwise gradient (10% methanol/ethyl acetate to 5% methanol/ethyl acetate in 2% intervals)

Method 2:

2'-deoxy-5'-tert-butyldiphenylsilyl dNTPs prepared as detailed above are reacted directly with the acid anhydride of the fluorochrome-photolabile linker conjugate in dry pyridine in the presence of 4-dimethylaminopyridine (DMAP) at 25° C. for 6 hours. The pyridine is then removed under vacuum, the residue is dissolved in deionized water, extracted in chloroform, washed with deionized water, with 10% HCl, saturated $NaHCO_3$, saturated NaCl, dried over $Na_2SO_4$, and purified by flash chromatography.

Method 3:

2'-deoxy-5'-tert-butyldiphenylsilyl dNTPs are dried by repeated co-evaporation with pyridine, dissolved in hot DMF and cooled to 0° C. in an ice bath. NaOH is dissolved in DMF after washing with dry benzene, then added to the dissolved 2'-deoxy-5'-tert-butyldiphenylsilyl and stirred for 45 minutes. A halogenated derivative of the fluorochrome-photolabile linker conjugate in DMF is added and the reaction is stirred for a few hours. The reaction is then quenched with cold deionized water and stirred overnight. The solid obtained is filtered, dried, and recrystallized in ethanol.

Method 4:

The 3'-caged NTPs can be prepared directly from the triphosphate according to Hiratsuka et al., *Biochim Biophys Acta* 742: 496-508 (1983).

In the case of methods 1-3, the resulting compounds are subsequently desolated by the addition of 1.0 equivalents of tetrabutylammonium fluoride ($Bu_4NF$). The reactions are monitored by thin layer chromatography and after completion (about 15 minutes), the reactions are quenched with 1 equivalent of glacial acetic acid. The solvent is removed, and the residues purified by silica column chromatography. The 5'-triphosphate derivatives of the compounds generated by methods 1-3 are synthesized by the following protocol. The 3'-modified nucleoside (1.0 equivalents) is dissolved in trimethylphosphate under a Nitrogen atmosphere. Phosphorus oxychloride ($POCl_3$) (3.0 equivalents) is added and the reaction is stirred at $-10°$ C. for 4 hours. The reaction is quenched with a solution of tributylammonium triphosphate (5.0 equivalents) in DMF and tributylamine. After stirring vigorously for 10 minutes, the reaction is quenched with TEAB pH 7.5. The solution is concentrated, and the triphosphate derivative isolated by linear gradient (0.01 M to 0.5 M TEAB) using a DEAE cellulose ($HCO_3$— form) column.

The final synthetic products are purified by HPLC, and may be further purified by enzymatic mop-up if necessary [Metzker, et al., *Biotechniques* 25: 814-817 (1998)], a technique which utilizes the extreme enzymatic preference of many polymerases for deoxynucleotides versus their 3'-blocked counterparts. This probably results from low efficiency of the catalytic formation of the phosphodiester bond when 3'-modified nucleotides are present in the enzyme active site so that the enzyme tends to rapidly exhaust the normal contaminating deoxynucleotides first. Brandis, et al., *Biochemistry* 35: 2189-2200 (1996).

In an alternative configuration a photolabile group is attached to the 3'-OH using succinimide or other chemistry and a fluorochrome-photolabile linker conjugate is attached directly to the base of the nucleotide as described by Anasawa et al., WO 98/33939. The 3' attached photolabile group will serve as a reversible chain terminator [Metzker, et al., *Nucleic Acids Res* 22: 4259-4267 (1994)] and the base-attached fluorochrome-photolabile linker will serve as a removable label. In this configuration with each cycle both photolabile groups will be removed by photolysis before further incorporation is allowed. Such a configuration may be preferred if it is found that steric hindrance of large fluorochrome groups attached to the 3'-OH of the nucleotide prevent the nucleotide from entering the polymerase.

EXAMPLE 4

DNAS Using a Cloned Hexahistidine-Tagged DNA Polymerase, Random Primed Single-Stranded DNA Template and Total Internal Reflection Fluorescence Microscopy There are two phases to the process.

Phase 1:

The first phase is the set-up phase. Hexahistidine-tagged DNA polymerase is washed into the reaction chamber and allowed to attach to the $Ni^{2-}$ nitrilotriacetic array. As an example, hexahistidine-tagged DNA polymerase from *Thermus aquaticus* might be used. Dabrowski, et al., Acta Biochim Pol 45: 661-667 (1998). Template DNA, is prepared by shearing or restriction digestion, followed by denaturation at 95° C. and annealing with a mixture of random oligodeoxynucleotide primers. The primed single-stranded DNA template is then pumped into the reaction chamber.

Phase 2:

The second phase of the process is the main sequencing cycle. The cycle is as follows:

1. Reaction buffer containing labeled-caged chain-terminating deoxynucleoside triphosphates (dNTP*s) is pumped into the reaction chamber. Reaction buffer consists of: 10 mM Tris HCl, pH 8.3; 50 mM KCl; and 2.5 mM $MgCl_2$. The dNTP*s are each at a concentration of 0.02-0.2 mM.
2. Reaction buffer without the dNTP*s is rinsed through the reaction chamber.
3. For each of the 10,000 reaction centers, the identity of the newly incorporated nucleotide is determined by total internal reflection fluorescence microscopy (TIRFM). Multiple recordings of the reaction center array are made so that each of the four nucleotides are distinguished. The fluorochromes used have high extinction coefficients and/or high quantum-yields for fluorescence. In addition, the fluorochromes have well resolved excitation and/or emission maxima. There are several fluorochrome families that will be used, for example, the BODIPY family of fluorochromes (Molecular Probes, Inc.). Using BODIPY fluorochromes and the photolabile linker 1-(4,5-dimethoxy-2-nitrophenyl) ethyl (DMNPE) the follow set of nucleotide analogs can be employed for DNAS:

3'-O-(DMNPE-($BODIPY^{493/503}$))-2' deoxy ATP
   3'-O-(DMNPE-($BODIPY^{530/550}$))-2' deoxy CTP
   3'-O-(DMNPE-($BODIPY^{564/570}$))-2' deoxy GTP
   3'-O-(DMNPE-($BODIPY^{581/591}$))-2' deoxy TTP Thus incorporated 'A's are detected with 488 nm Argon-ion laser illumination and a barrier filter centered at 503 nm. Incorporated and 'C's, 'G's and 'T's with are detected with 532 nm YAG laser illumination and barrier filters centered at 550 nm, 570 nm, and 591 nm respectively.

For each of the separate illumination events an evanescent wave is generated in the reaction center array and the image of the array is focused through the microscope system onto the face of a micro-channel plate intensified cooled-CCD camera.
4. Newly incorporated nucleotides are optically uncaged by illumination with <360 nm light from another YAG laser. This causes dissociation of the DMNPE-BODIPY from the nascent nucleic acid strand leaving it intact and prepared to incorporate the next nucleotide.
5. The removal of the fluorescent moiety is verified by TIRFM and the reaction cycle is repeated until nucleotides are no longer incorporated.

Typically, the exposure time for each fluorochrome is 100 msec. The readout time of the CCD chip is ~0.25 sec. Hence, the detection step for each cycle takes <1.5 secs. The total volume of the reaction chamber is 1-10 µl. Less than one second is taken to completely flush the reaction chamber. Hence the total time for a given cycle is less than 10 seconds. Therefore, at 10 seconds/cycle each of the 10,000 reaction centers of the DNAS machine is able to deduce at least 360 bases of sequence per hour, corresponding to 3.6 M base/hour of sequence deduced by the DNAS machine as a whole.

Shutters controlling laser illumination, filter wheels carrying the barrier filters and the CCD camera are all controlled by a microcomputer. Image collection and data analysis are all executed by the same microcomputer. Extracted sequence data and array images are stored permanently on CD ROM as they are collected.

EQUIVALENTS

From the foregoing detailed description of the specific embodiments of the invention, it should be apparent that a unique method and apparatus for nucleic acid sequencing has been described. Although particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made to the invention without departing from the spirit and scope of the invention as defined by the claims. For instance, the choice of the particular polymerase, the particular linkage of the polymerase to the solid support, or the particular nucleotide terminators is believed to be a matter of routine for a person of ordinary skill in the art with knowledge of the embodiments described herein.

The invention claimed is:

1. A method for nucleotide base sequencing comprising the sequential steps of:
   (a) immobilizing a plurality of polymerases on a solid support in the absence of nucleic acid wherein each polymerase is immobilized in a reaction center of said solid support, and wherein said solid support comprises a plurality of reaction centers each containing a single polymerase located at an optically resolvable distance from each other;
   (b) providing a single nucleic acid sample for each of the plurality of said polymerases and a plurality of different oligonucleotide primers, wherein each of the nucleic acid sample hybridizes to a single oligonucleotide primer;
   (c) providing four different nucleotides, each nucleotide being differentially-labeled with a detachable labeling group and blocked at the 3' portion with a detachable blocking group, wherein the polymerase extends the primer hybridized to the nucleic acid sample with a single differentially-labeled nucleotide that is complementary to the sample nucleic acid thereby creating a single detachable labeling group attached to the solid support;
   (d) removing nucleotides that have not been incorporated in the primer;
   (e) detecting the single labeled nucleotide incorporated into the elongating primer in each of reaction centers by detecting the single labeling group attached to the solid support, thereby identifying the complement of the labeled 3'-blocked nucleotide at each said reaction center;
(f) separating the 3' blocking group and the labeling group from the incorporated nucleotide;
(g) removing the separated 3' blocking group and the separated labeling group of step (f) to produce an unlabeled nucleic acid sample;
(h) confirming separation and removal of the 3' blocking group from the nucleotide incorporated in the primer of each reaction center by detecting for the presence of the single labeled nucleotide in each of the reaction centers wherein the presence of a labeled nucleotide indicates that the step of separating the labeling group from the incorporated nucleotide was not successful; and
(i) repeating steps (c) through (h) until either no new nucleotides are incorporated in step (c) or the 3' blocking group persists in not being separated and removed in steps (f) and (g),
whereby the order in which the labeled nucleotides in step (e) are detected in a reaction center corresponds to the complement of the sequence of at least a portion of the nucleic acid sample in that reaction center.

2. The method of claim 1, wherein the 3' blocking group and the labeling group are separated from the incorporated nucleotide by photochemical activation.

3. The method of claim 1, wherein the 3' blocking group and the labeling; group are separated from the incorporated nucleotide by chemical or enzymatic activation.

4. The method of claim 1, wherein the differentially-labeled labeling group is a fluorescent label, a plasmon resonant particle, or a quantum dot label.

5. The method of claim 1, wherein the labeling group is directly attached to the detachable 3' blocking group.

6. The method of claim 5, wherein the detachable 3' blocking group is a 2-Nitrobenzyl group.

7. The method of claim 1, wherein the labeling group is attached to the base of each nucleotide with a detachable linker.

8. The method of claim 7, wherein the detachable linker is a 2-Nitrobenzyl group.

9. The method of claim 1, wherein the polymerase is selected from the group consisting of DNA polymerase, RNA polymerase, and reverse transcriptase.

10. The method of claim 9, wherein the DNA polymerase is selected from the group consisting of the DNA polymerase from *Bacillus stearothermophilus*, the DNA polymerase from *Thermus acquaticus*, the DNA polymerase from Pyrococcusfuriosis, the DNA polymerase from *Thermococcus litoralis*, the DNA polymerase from *Thermus thermophilus*, the DNA polymerase from bacteriophage T4, the DNA polymerase from bacteriophage T7, the *E. coli* DNA polymerase I Klenow fragment, and *E. coli* DNA polymerase III.

11. The method of claim 9, wherein the RNA polymerase is selected from the group consisting of the RNA polymerase from *E. coli*, the RNA polymerase from the bacteriophage T3, the RNA polymerase from the bacteriophage T7, the RNA polymerase from the bacteriophage SP6, and the RNA polymerases from the viral families of bromoviruses, tobamoviruses, tombusvirus, leviviruses, hepatitis C-like viruses, and picornaviruses.

12. The method of claim 9, wherein the reverse transcriptase is selected from the group consisting of the reverse transcriptase from the Avian Myeloblastosis Virus the reverse transcriptase from the Moloney Murine Leukemia Virus, the reverse transcriptase from the Human Immunodeficiency Virus-1, and modified T7 polymerase.

13. The method of claim 1, wherein the labeled nucleotide is detected by the detection method selected from the group consisting of total internal reflection fluorescence microscopy, photon confocal microscopy, surface plasmon resonance, and fluorescence resonance energy transfer.

* * * * *